(12) United States Patent
Batuman et al.

(10) Patent No.: US 8,754,094 B2
(45) Date of Patent: Jun. 17, 2014

(54) METHODS FOR HEAT SHOCK PROTEIN DEPENDENT CANCER TREATMENT

(75) Inventors: Olcay Batuman, New York, NY (US); Jeffrey L. Brodsky, Pittsburgh, PA (US)

(73) Assignees: The Research Foundation of State University of New York, Albany, NY (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 962 days.

(21) Appl. No.: 12/673,397

(22) PCT Filed: Aug. 15, 2008

(86) PCT No.: PCT/US2008/073356
§ 371 (c)(1),
(2), (4) Date: Mar. 18, 2011

(87) PCT Pub. No.: WO2009/023846
PCT Pub. Date: Feb. 19, 2009

(65) Prior Publication Data
US 2011/0160160 A1    Jun. 30, 2011

Related U.S. Application Data

(60) Provisional application No. 60/956,015, filed on Aug. 15, 2007.

(51) Int. Cl.
*A61K 31/513* (2006.01)

(52) U.S. Cl.
USPC ........................................................ 514/274

(58) Field of Classification Search
None
See application file for complete search history.

(56) References Cited

U.S. PATENT DOCUMENTS

| | | | |
|---|---|---|---|
| 6,096,711 A | 8/2000 | Sherman et al. | |
| 6,855,802 B1 | 2/2005 | Triebel et al. | |
| 6,984,389 B2 | 1/2006 | Li | |
| 7,179,462 B2 | 2/2007 | Srivastava et al. | |
| 2003/0129196 A1 | 7/2003 | Srivastava | |
| 2004/0253228 A1 | 12/2004 | Srivastava | |
| 2005/0009771 A1 | 1/2005 | Levanon et al. | |
| 2005/0043233 A1 | 2/2005 | Stefanic et al. | |
| 2006/0052390 A1 | 3/2006 | Schreiner et al. | |
| 2006/0058311 A1 | 3/2006 | Munzert et al. | |
| 2006/0160109 A1 | 7/2006 | MacDonald et al. | |
| 2006/0166947 A1 | 7/2006 | Anderson et al. | |
| 2006/0205757 A1 | 9/2006 | Zhang et al. | |
| 2006/0239909 A1 | 10/2006 | Anderson et al. | |
| 2006/0252740 A1 | 11/2006 | Johnson, Jr., et al. | |
| 2006/0293358 A1 | 12/2006 | Dinsmore et al. | |
| 2007/0072860 A1 | 3/2007 | Bruncko et al. | |
| 2007/0105862 A1 | 5/2007 | Bruncko et al. | |
| 2009/0062222 A1* | 3/2009 | Sherman et al. | 514/34 |

OTHER PUBLICATIONS

Wright et al. Bioorganic & Medicinal Chemistry, 2008, vol. 16, pp. 3291-3301.*
Wisen et al. Bioorg. Med. Chem. Lett., 2008, vol. 18, pp. 60-65.*
Garrido et al. Cell Cycle, 2003, vol. 2, No. 6, pp. 579-584.*
Munshi et al. Blood, 2003, vol. 103, pp. 1799-1806.*
Fewell, Sheara W., et al., "Small molecule modulators of endogenous and co-chaperone-stimulated Hsp70 ATPase activity", The Journal of Biological Chemistry, vol. 279, No. 49, pp. 51131-51140, 2004.
Nylandsted, Jesper et al., "Selective depletion of heat shock protein 70 (Hsp70) activates a tumor-specific death program that is independent of caspases and bypasses Bcl-2", PNAS, vol. 97, No. 14, pp. 7871-7876, 2000.
International Search Report for International Application No. PCT/US2008/073356 dated, Jan. 8, 2009.

* cited by examiner

*Primary Examiner* — James D Anderson
(74) *Attorney, Agent, or Firm* — Hoffmann & Baron, LLP

(57) ABSTRACT

The present invention provides a method of treating an Hsp70 dependent cancer, including: providing at least one Hsp70 dependent cancer cell; contacting the at least one cell with a sub-effective concentration of a dihydropyrimidinone compound; and contacting the at least one cell with a sub-effective concentration of a proteasome inhibitor, wherein the sub-effective concentration of the dihydropyrimidinone compound and the sub-effective concentration of the proteasome inhibitor have a synergistic effect upon the at least one cell.

7 Claims, 41 Drawing Sheets

4a: R¹=2-thiophene, R²=Bn, R³=Me, n=1; 33% (93% purity)
4b: R¹=4-NO₂C₆H₄, R²=Bn, R³=Me, n=1; 84% (92% purity)
4c: R¹=4-PhC₆H₄, R²=Bn, R³=Me, n=3; 83% (94% purity)
4d: R¹=4-BrC₆H₄, R²=Et, R³=Me, n=1; 68% (99% purity)
4e: R¹=2-ClC₆H₄, R²=Bn, R³=Me, n=3; 80% (84% purity)

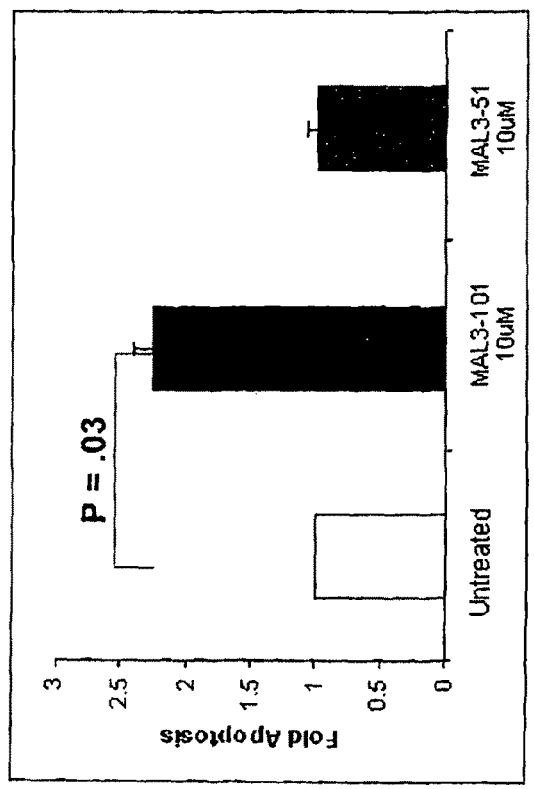
FIG. 25A
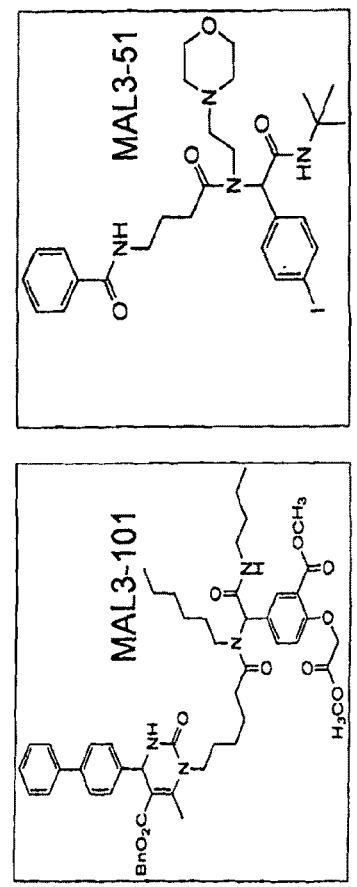
FIG. 25B
FIG. 25C

Table of MG-132 + MAL3-101 Syngergy

| MG-132 (µM) | MAL3-101 (µM) | Viability (%) | $F_a$ | CI |
|---|---|---|---|---|
| 0.01 | 0.01 | 41 | 0.595 | 0.005 |
| 0.03 | 0.03 | 23 | 0.768 | 0.006 |
| 0.07 | 0.07 | 17 | 0.827 | 0.008 |
| 0.10 | 0.10 | 17 | 0.831 | 0.011 |

FIG. 30

Table of 17-AAG + MAL3-101 Syngergy

| 17-AAG (µM) | Viability +MAL5 (%) | $F_a$ +MAL 5µM | CI +MAL 5 µM | 17-AAG (µM) | Viability +MAL10 (%) | $F_a$ +MAL 10 µM | CI +MAL 10µM |
|---|---|---|---|---|---|---|---|
| 0.025 | 86 | 0.13 | 0.29 | 0.025 | 50 | 0.50 | 0.07 |
| 0.05 | 74 | 0.26 | 0.30 | 0.05 | 44 | 0.66 | 0.08 |
| 0.1 | 73 | 0.27 | 0.57 | 0.1 | 28 | 0.72 | 0.13 |
| 0.5 | 28 | 0.72 | 0.64 | 0.5 | 3 | 0.97 | 0.09 |
| 1.0 | 8 | 0.92 | 0.41 | 1.0 | 2 | 0.98 | 0.12 |

FIG. 31

Table of Summarized of IC Values

| | IC$_{30}$ (µM) | IC$_{50}$ (µM) | IC$_{70}$ (µM) |
|---|---|---|---|
| MAL3-101 | 5.9 | 8.3 | 22.6 |
| MG-132 | 0.65 | 1.7 | 3.7 |
| MAL + MG | 0.005 | 0.008 | 0.22 |
| 17-AAG | 0.22 | 0.40 | 0.83 |
| MAL 5 µM + AAG | 0.13 | 0.30 | 0.48 |
| MAL 10 µM + AAG | 0.02 | 0.03 | 0.08 |

FIG. 32

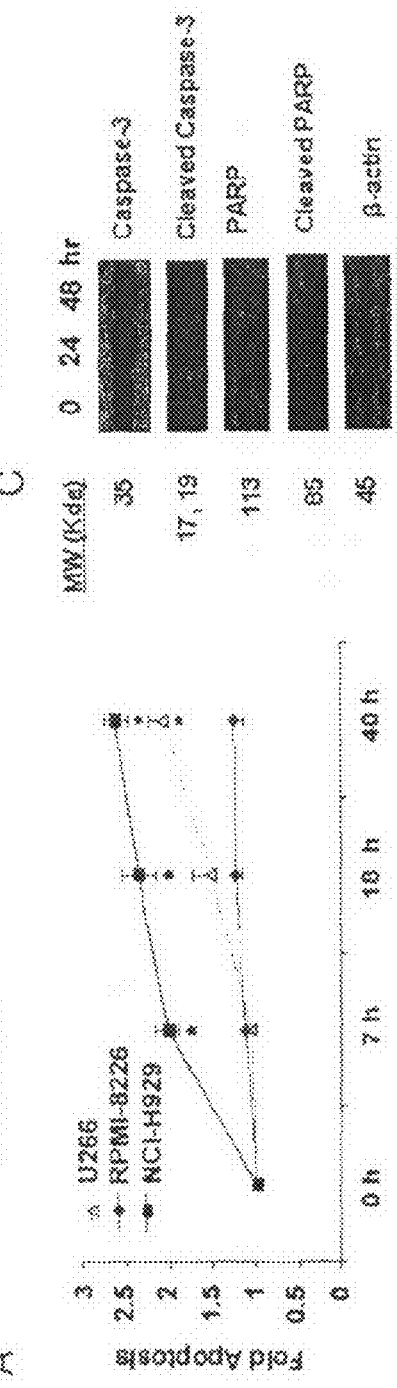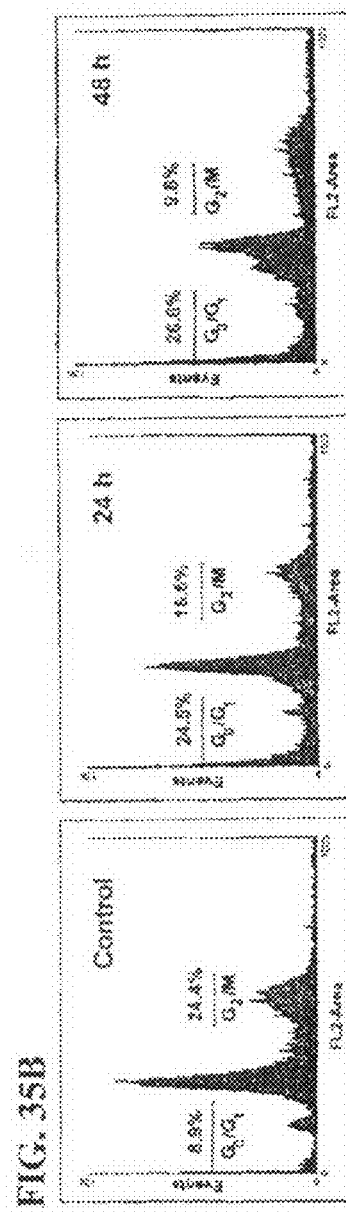

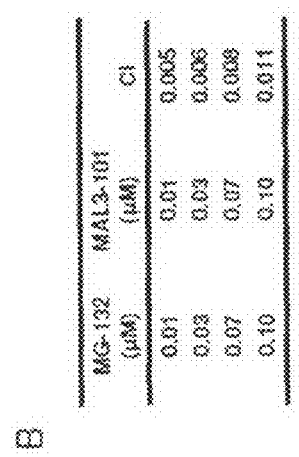
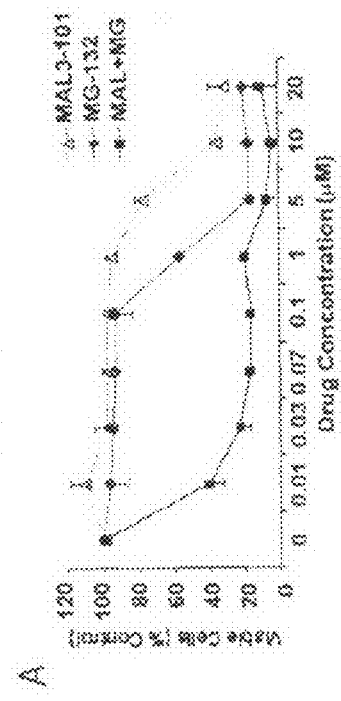
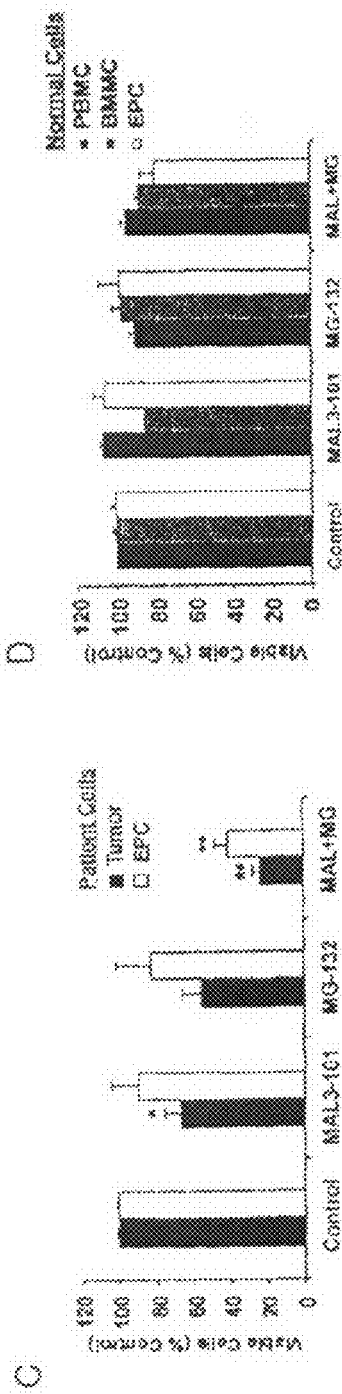
FIG. 36A
FIG. 36B
FIG. 36C
FIG. 36D

Table Depicting Weight of Light Chain (LC) Immunoglobulin Secreted
By Various Multiple Myeloma Cell Lines

Table 1

| MM cell line | Light Chain (LC) produced | Secreted LC (ng/10⁶ cells) | Intracellular LC (ng/10⁶ cells) | Relative LC secretion (Secreted / Intracellular) |
|---|---|---|---|---|
| NCI-H929 | κ | 505 ± 22 | 93 ± 9.9 | 5.46 ± 0.4 |
| U266 | λ | 639 ± 30 | 387 ± 32 | 1.66 ± 0.2 |
| RPMI-8226 | λ | 56 ± 51 | 1271 ± 18 | 0.16 ± 0.1 |

FIG. 39

Table Depicting Treatments of NCI-H929 Multiple Myeloma Cell Line and Various IC Values Recorded Therefor

Supplementary Table

| Treatment of NCI-H929 | $IC_{50}$ (µM) at 40 h |
|---|---|
| Single agents | |
| MAL3-101 | 8.3 |
| MG-132 | 1.7 |
| 17-AAG | 0.40 |
| Combinations | |
| MAL3-101 + MG-132 | 0.008 |
| MAL3-101 + 17-AAG | 0.03 |

FIG. 40

METHODS FOR HEAT SHOCK PROTEIN DEPENDENT CANCER TREATMENT

CROSS-REFERENCE TO RELATED APPLICATIONS

This application is the National Stage of International Application No. PCT/US08/73356, filed Aug. 15, 2008, which claims priority to U.S. Provisional Patent Application No. 60/956,015, filed on Aug. 15, 2007, the contents of each of which are incorporated by reference herein in their entireties.

GOVERNMENT FUNDING STATEMENT

This invention was supported by U.S. government funds, via grant awarded by the National Cancer Institute of the National Institutes of Health under Grant No. 5R21CA11583202. As such, the government has certain rights to this invention.

TECHNICAL FIELD

The present invention relates to methods and compositions for treating certain types of heat shock protein dependent cancers. Specifically, the present invention relates to methods of using a class of compounds which have Hsp70 inhibiting effects to diagnose, treat, or provide therapeutic effects to certain types of cancer cells.

BACKGROUND OF THE INVENTION

Many forms of cancer remain fatal despite advances in medical research and treatment. For example, multiple myeloma (MM) is a type of bone cancer that, despite advances in medical treatment, remains fatal.

Although there are several treatments for the disease, MM has proven difficult to acquire long-term remissions, and patients have an overall median survival of three to five years. One treatment method in current use is proteasome inhibition therapy, using, for example, Bortezomib (clinically Bortezomib, in the lab MG-132). While Bortezomib treatments have shown clinical effects on some patients diagnosed with MM, up to 12% of patients treated show no response to Bortezomib. Also, up to 30% of patients treated with Bortezomib exhibit neuropathy. Furthermore, MM has a high refractory and relapse nature and anywhere from 20% to 60% of relapsed patients who were previously treated with Bortezomib do not respond to subsequent therapies. Research has shown that some cancers, including, for example, MM, are resistant to anti-cancer effects of Bortezomib due to various mechanisms that include an increase in production of the heat shock proteins within cancer cells which can mitigate the effects of Bortezomib. Therefore, cancer cells may be initially unresponsive or eventually grow resistant to Bortezomib treatment by mechanisms that involve heat shock protein production within these cells.

Patients typically cannot be given high doses of Bortezomib in order to improve the response, as the drug is highly toxic. Also, increased dosages may induce drug resistance and/or refractiveness to treatment in cancer patients. Due to the prognosis and projected life span of current MM patients, the long-term toxicity issues to patients undergoing proteasome inhibitor treatment are a secondary concern to surviving the cancer. Thus, Bortezomib, although an excellent agent to induce some response in MM patients, lacks important properties to be used as an effective long term agent to prolong survival and achieve cure in the treatment of MM. Inadequate treatment currently exists for other types of cancer sharing one or more characteristics with MM.

SUMMARY OF THE INVENTION

An aspect of the present invention provides a method of treating an Hsp70 dependent cancer, including: providing at least one Hsp70 dependent cancer cell; contacting the at least one cell with a sub-effective concentration of a dihydro pyrimidinone compound; and contacting the at least one cell with a sub-effective concentration of a proteasome inhibitor, wherein the sub-effective concentration of the dihydro pyrimidinone compound and the sub-effective concentration of the proteasome inhibitor have a synergistic effect upon the at least one cell.

Another aspect of the present invention provides a method of treating MM, including: providing a plurality of MM cells, co-administering a sub-effective concentration of each of a Hsp70 inhibitor and a proteasome inhibitor to the plurality of cells, wherein the sub-effective concentrations of the Hsp70 inhibitor and the proteasome inhibitor together have a synergistic apoptotic effect on the MM cells.

Yet another aspect of the present invention provides a method of treating MM, including: co-administering a sub-effective concentration of an Hsp70 inhibitor and a sub-effective concentration of a proteasome inhibitor, wherein the Hsp70 inhibitor and the proteasome inhibitor have a synergistic effect on both the tumor and its microvasculature.

Still yet another aspect of the present invention provides a combination therapy for a plurality of Hsp70 dependent cancer cells, including: a sub-effective concentration of an Hsp70 inhibitor; a sub-effective concentration of a proteasome inhibitor; and a biologically compatible delivery means.

Yet another aspect of the present invention provides a composition of matter, including: an Hsp70 inhibitor; and a proteasome inhibitor, each of the Hsp70 inhibitor and the proteasome inhibitor are in a pharmaceutically acceptable carrier, wherein the Hsp70 inhibitor and the proteasome inhibitor in the carrier are administrable to a plurality of Hsp70 dependent cancer cells.

A further aspect of the present invention provides a method of screening Hsp70 inhibitors, including: administering to at least one Hsp70 dependent cancer cell an amount of a candidate Hsp70 inhibitor; and assaying the at least one cell to determine whether Hsp70 is inhibited.

Still another aspect of the present invention provides: a method of diagnosing a progression of Hsp70-dependent cancer, including: providing a sample of Hsp70 dependent cancer cells from a subject; assaying the sample to determine a quantity of secreted immunoglobulins; correlating the quantity of secreted immunoglobulins to a standard. This will provide an assessment whether the patient may be a candidate to receive treatment with Hsp70 antagonists.

Another aspect of the invention provides a method for determining a therapy for a MM patient in need thereof, including: providing a sample of MM cells from a subject; assaying the sample to determine a quantity of secreted immunoglobulins; correlating the quantity of secreted immunoglobulins to a standard; wherein each quantity is assigned to a level of MM, wherein a high level correlates to an aggressive MM, while a low level correlates to a less aggressive MM.

Another aspect of the present invention provides an Hsp70 dependent cancer treatment, including: an Hsp70 inhibitor in a concentration range from 0.01 µM to 0.1 µM; and a proteasome inhibitor, a concentration range from 0.01 µM to 0.1

μM. Optionally, the Hsp dependent cancer treatment may further comprise an Hsp90 inhibitor and/or a solvent to solubilized the inhibitors.

Yet another aspect of the present invention provides a multiple myeloma treatment mixture, including: a MAL3-101 in a concentration range from about 0.01 μM to about 0.1 μM; a MG-132 in a concentration range from about 0.01 μM to about 0.1 μM. Optionally, an Hsp90 inhibitor in a concentration amount of 0.025 μM to 10 μM and/or a delivery means configured to increase a bioactivity of the inhibitors.

The various embodiments of the present invention relate to a class of small molecule Hsp70 modulators which may be used in sub-effective concentrations with one or more additional components to treat one or more types of Hsp70-dependent cancers, including for example, MM, lung cancer, breast cancer, cervical cancer, and colon cancer. These and other features of the invention will be better understood through a study of the following detailed description, claims, and accompanying drawings.

BRIEF DESCRIPTION OF THE DRAWINGS

FIG. 25A is experimental data summarized in a chart which depicts the apoptotic response of untreated cells, cells treated with MAL3-101, and cells treated with a negative control, MAL3-51, plotted as fold apoptosis versus treatment (in micromolar).

FIG. 25B is a representation of Hsp70 inhibitor MAL3-101.

FIG. 25C is a representation of a negative control compound MAL3-51.

FIG. 30 is a table of experimental data depicting the synergistic effect of Hsp70 inhibitor (MAL3-101) and proteasome inhibitor (MG-132) combined treatments at levels that are sub-effective when added alone.

FIG. 31 is a table of experimental data depicting the synergistic effect of Hsp70 inhibitor (MAL3-101) and Hsp90 inhibitor (17-AAG) combined treatments at levels that are sub-effective when added alone.

FIG. 32 is a table summarizing the IC values obtained by treating multiple myeloma cells with different inhibitors (Hsp70, Hsp90, and proteasome inhibitors) at different concentration levels either individually or in combination.

FIG. 35A shows a time course chart of MM cell lines which were exposed to 10 μM of MAL3-101 for 40 h and the fold change in apoptosis in MAL3-101-treated versus control, DMSO-treated cells as determined by flow cytometry.

FIG. 35B is experimental data which shows the percentages of NCI-H929 cells in the $G_0/G_1$ and $G_2/M$ phases of the cell cycle after 10 μM treatment with MAL3-101 for 40 h.

FIG. 35C depicts the results when NCI-H929 cells were exposed to 10 μM MAL3-101 for the indicated culture periods and immunoblotted with primary antibodies to detect caspase-3 and poly (ADP-ribose) polymerase (PARD), and, to ensure equal loading, β-actin.

FIG. 36A depicts experimental data in which NCI-H929 cells ($1 \times 10^5$) were exposed to the indicated concentrations of MAL3-101, MG-132, or a combination for 40 h and survival was assessed by an MTS assay; representative data from one of three independent experiments are shown; error bars represent SDs from replicate data points.

FIG. 36B depicts the fraction of non-viable cells compared to control, DMSO-treated cells in this experiment, which was used for isobologram analysis; combination index (CI) values <1 indicate synergy.

FIG. 36C depicts bone-marrow-derived tumor cells (black bars) and confluent endothelial progenitor cells (EPCs) (white bars) from multiple myeloma patients which were exposed to the indicated concentrations of MAL3-101, MG-132, or their combination, and survival was assessed by an MTS assay.

FIG. 36D depicts the normal peripheral blood mononuclear cells (PBMC, black bars), bone marrow mononuclear cells (BMMC, gray bars), and confluent bone-marrow-derived EPCs (white bars) which were exposed to the indicated concentrations of MAL3-101, MG-132, or a combination, and survival was assessed by an MTS assay.

FIG. 39 is a table depicting experimental data which shows that the multiple myeloma cell line NCI-H929 is a high secretor of monoclonal immunoglobulin.

FIG. 40 is a table depicting the comparison of the inhibitory concentration (IC) of MAL3-101 with other modulators of protein quality control (MG-132 and 17-AAG) alone and in combination in the multiple myeloma cell line NCI-H929.

DETAILED DESCRIPTION OF THE INVENTION

Figure 1:
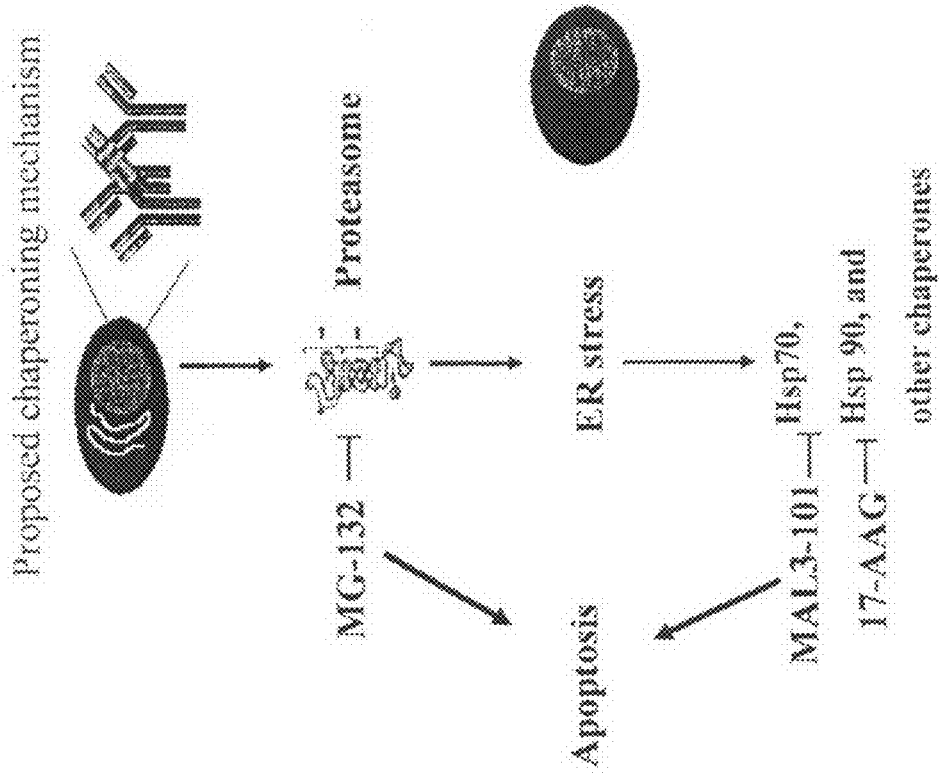
FIG. 1 depicts a proposed chaperoning mechanism related to the present invention.

With reference to FIG. 1, as discovered by the inventors of the present invention, one reason that Hsp70 dependent cancers cells, and specifically, multiple myeloma (MM) cells may be resistant to various drugs, including proteasome inhibitors, may be that cancer cells treated with these drugs undergo a heat shock response. A heat shock response may effectively upregulate various classes of heat shock proteins. Heat shock proteins may in turn protect the cancer cell from apoptosis and prevent the cell from undergoing programmed cell death. As such, the cancer cells survive and may become resistant to the drugs to the extent that the drugs become ineffective.

The various embodiments of the present invention include, inter alia, methods of treating certain Hsp-reliant or dependent cancer cells. The embodiments of the present invention solve the problems of toxicity of medicaments, ineffective treatments, and unavailable therapies to prolong a patient's life given a certain clinical course of Hsp reliance. The various embodiments as set forth herein provide methods for treating and diagnosing various forms of cancer. Such cancers include, for example, hematological malignancies such as MM. Although MM will be referenced and discussed, it is understood that the various embodiments of the present invention may be likewise used with other types of malignancies, particularly reliance upon heat shock proteins, including Hsp70. Some cancers which are currently believed to be heat shock reliant or dependent include, for example, certain forms of lung cancer, breast cancer, cervical cancer, colon cancer, and bone cancer.

In living cells, various mechanisms and cellular functions cooperate to provide for cell heath and longevity. When a cell encounters stress, including heat shock, oxidative stress, or exposure to chemicals, proteins within the cell's endoplasmic reticulum start to unfold and aberrant proteins accumulate. This, in turn, triggers an unfolded protein response (UPR). Proteins in the cytoplasm may undergo the same phenomenon under stress conditions. If aberrant proteins continue to accumulate, the cell will undergo apoptosis, programmed cell death. Once aberrant proteins begin to accumulate within the cell, the inventors of the present invention discovered that certain classes of heat shock proteins, or Hsps, were upregulated to effectively chaperone the cell and counteract stress.

One function common to virtually all living organisms is that of Hsp. Together, there are five different classes of Hsps, each with varying roles within the cell. Hsp70 and Hsp90 each represent two major classes of heat shock proteins. Hsp nomenclature is a function of the molecular weights of the various families in units of kilodaltons (kDa). Hsps in the Hsp70 family have an average molecular weight of 70 kDa; whereas, Hsp90 members have an average molecular weight of 90 kDa.

Hsp90 and Hsp70 exhibit differing roles within the cell. Without intending to be bound by a particular mechanism or theory, the following presents a non-limiting discussion of the roles of each of the classes of heat shock proteins within the cell, with reference to a cell stressor, like MG-132. Once a cell undergoes cell stress, such as that induced by a proteasome inhibitor, Hsp90 and Hsp70 are both upregulated in the cell, as shown in FIG. 1. Thus, in order to drive the cell towards apoptosis, an Hsp70 and an Hsp90 inhibitor may be applied individually or in combination to at least one cell.

Hsp90 may be considered by some to have a chaperoning effect. However, Hsp90 is most commonly known as responsible for maintaining the stability or completing the folding of steroid hormone receptors, and select protein kinases and transcription factors within the cell. In contrast, Hsp70 is commonly accepted as having a general chaperoning effect in the cell, as Hsp70 is responsible for folding and unfolding proteins as well as for providing thermotolerance to cells exposed to heat stress. Further, Hsp70 disposes of aberrant proteins and assists in the refolding of the proteins in the cytoplasm and endoplasmic reticulum in order to combat UPR induction and cytoplasmic stress, which ultimately would result in apoptosis. In cells where Hsp90 is present, Hsp70 is also present, and as discussed, the two chaperones partially compensate for one another but Hsp70 has a much stronger global chaperoning effect.

Monomeric Hsp70 binds to short peptides of hydrophobic character, and Hsp40s entrap the peptides onto Hsp70 by stimulating Hsp70 ATP hydrolysis. Hsp70s will bind to almost all proteins (as the protein interior is of hydrophobic character). As a result, Hsp70s are involved in protein folding, degradation, transport, and the maturation of multi-protein complexes. In contrast, dimeric Hsp90 binds to proteins that already have some partial structure, and their roles in protein biogenesis seem confined to those specialized substrates that have already begun to mature (i.e., Hsp70 acts before Hsp90 in the folding pathway). Although Hsp90 is also an ATPase, this activity is not enhanced by Hsp40s but instead is altered by other co-chaperones (e.g. Hop, Hip, and Aha1). Hsp90 substrates include some kinases, transcription factors, and steroid hormone receptors, and it has been shown that substrates that require Hsp70 for folding or degradation do not necessarily employ Hsp90, and vice versa. Also, depending on the tumor line, Hsp70 and/or Hsp90 are anti-apoptotic and are required for tumor survival. While a breast cancer cell line requires Hsp70 but not Hsp90 for survival, in contrast a small cell lung carcinoma requires Hsp90 but not Hsp70 for survival.

Hsp70 and Hsp90 inhibitors function differently within the cell in order to inhibit each class of heat shock proteins. Hsp90 inhibitors (e.g. 17-AAG and GA) function by interacting with the ATP binding cleft in the chaperone, which is relatively unique. In effect, the ATP is contorted in this binding site and the Hsp90 inhibitors mimic this conformation and, as thus, exclude ATP from the chaperone. In contrast, the ATP binding site in Hsp70 resembles that in actin (and is thus not unique). The Hsp70 inhibitors may bind to the underside of the ATPase domain (but not in the ATP binding cleft) in Hsp70. Thus, the proteins are quite distinctive (there is no homology between them) and the inhibitors function uniquely with each chaperone class.

The research of the present inventors was directed to understanding the chaperoning mechanism of Hsp70 in various Hsp dependent cancer cell lines, particularly multiple myeloma, while undergoing various forms of treatment and therapy. By gaining an understanding into the mechanism itself, the present inventors have been able to direct methods for treatment, methods for screening medicaments, and methods for diagnosing the type of cancer, providing a composition of matter, providing a combination therapy, as well as the best type of therapy for a subject. Cancer cells, like healthy cells, upregulate Hsp70 when they are under stress. This can occur when drugs are administered that are designed to kill the cancer. Thus, upregulation of Hsp70 in various types of cancer cells acts to shield the cancer cells from treatment. Therefore, many drugs and therapies may result in ineffective treatment, and little therapeutic affects on the subject. As Hsp70 protects cancer cells from apoptosis, so too may the Hsp70 chaperoning effect facilitate the longevity of cancer cells. The research related to the present invention focused on, among other things, understanding how cancer cells may be resistant to common cancer treatments, new medicaments, and other approaches.

Figure 33:
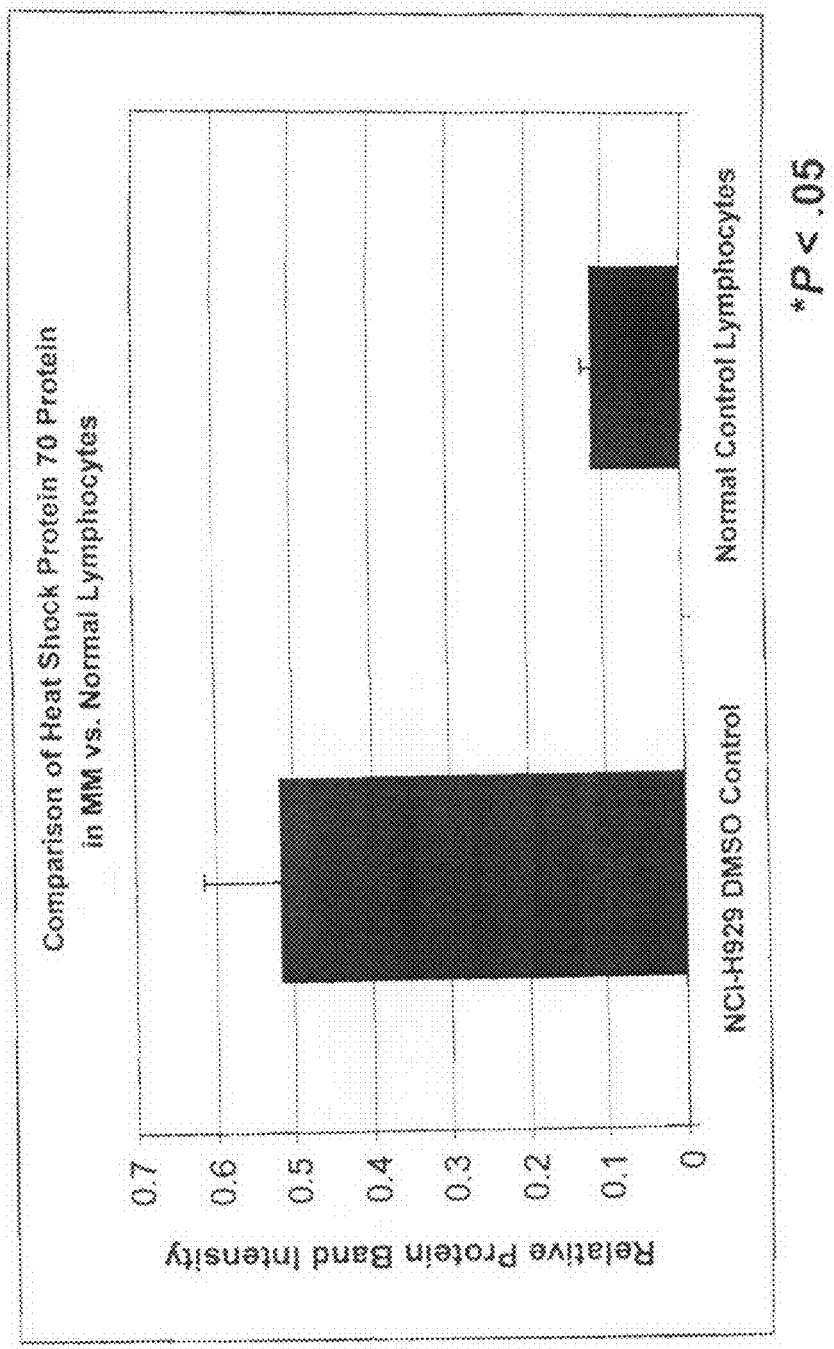
FIG. 33 is experimental data depicting the quantified data from western blot analyses of Hsp70 present in multiple myeloma cell lines compared to normal lymphocytes from at least three experiments.

Cancer cells, unlike normal cells, are very dependent on Hsp70 in order to survive. Research of the present inventors has shown that in certain cancer cells (i.e., multiple myeloma), Hsp70 gene and protein expression are upregulated on a greater level when compared to normal plasma cells. With reference to the chart of Relative Protein Band Intensity versus Type of Cell in FIG. 33, the difference in Hsp 70 in NCI-H929, a multiple myeloma cell line, versus normal lymphocyte cells, is clearly depicted. The Western Blot analysis of both cell samples from at least three experiments demonstrate that there is well over four times as much Hsp70 (Fold=4.5) in the multiple myeloma cell line (approximately 0.51) than in normal lymphocyte cells (approximately 0.11). Therefore, the present inventors have discovered that by inhibiting the Hsp70 upregulation, the cancer cell is left susceptible to the targeted treatment, while normal cells are relatively unaffected. As Hsp70 is much more prevalent in multiple myeloma cells than in healthy cells, the cancer cells are thus more susceptible than the surrounding normal, healthy cells to the Hsp70 inhibitors. Further, it has been determined that certain Hsp70 inhibitors may be used individually, or in combination with proteasome inhibitors, Hsp90 inhibitors, or even other cancer therapies and treatments in order to provide an effective treatment. By inhibiting Hsp70 upregulation in cancer cells, the drugs designed to cause apoptosis in the cancer cells, like proteasome inhibitors, may have an increased effectiveness. Thus, Hsp70 inhibitors may be used in lower drug dosages, fewer treatment cycles, and with fewer overall occurrences of relapse or refractory cancer (drug resistance or cancer that is unresponsive to treatments).

Some types of cancer that are dependent on the Hsp70 chaperoning mechanism include breast cancer, certain hematological malignancies, and other cancers. Hematological malignancies, or blood cancers, are cancers which affect the blood, bone marrow, and lymph nodes and may include, for example, leukemia, lymphoma, and multiple myeloma. Other Hsp70 dependent cancers include, for example, non-Hodgkin's lymphoma, glioblastoma, and colon cancer cells.

Multiple myeloma (also referred to as MM) is the second most commonly diagnosed blood cancer. MM is a bone marrow cancer that affects the bone marrow stromal cells in patients, and causes detrimental affects to various organs including bone marrow, bones and kidneys and vital bodily functions. Specifically, MM affects the plasma cells (part of the immune system) which produce antibodies. Despite ongoing research in the cancer field, MM remains both incurable and fatal. The average life expectancy of a patient diagnosed with MM is around 4-10 years. Median survival of patients diagnosed with MM is two to five years, with roughly 50% of patients expected to remain alive. As multiple myeloma is a difficult cancer to radically treat in at least a large subset of patients, treatment typically focused on containment and suppression, not eradication. MM patients commonly relapse after treatment. In relapse, multiple myeloma often exhibits refractory and resistance characteristics, which makes the relapse more difficult to treat than the initial onset.

As discussed, proteasome inhibitor therapy is one common treatment for MM patients. The proteasome is an enzyme complex that exists in all cells and is vital in, among other important cellular processes, cell apoptosis. Many of the processes that rely on proteasome function can contribute to the growth and survival of cancer cells. Proteasomes are present in all cells and function to help regulate cell growth. Proteasome regulates protein expression and cleans normal cells, as well as cancer cells, of abnormal or misfolded proteins. Thereby, proteasome inhibition in cancer cells disrupts many cellular processes, thus propagating pro-apoptotic factors to activate programmed cell death. Upon treatment of both normal and cancer cells with proteasome inhibitors, normal cells appear to be able to recover from intermittent proteasome inhibition, but many types of cancer cells undergo apoptosis (programmed cell death) when proteasomes are inhibited, even for a short time.

Proteasome inhibitors, including Bortezomib or MG-132, display several negative side effects in its use. Bortezomib cause peripheral neuropathy (nerve damage to peripheral nervous system) in approximately 30% of patients. In addition, myelosuppression as neutropenia (hematological disorder of an abnormally low number of a type of while blood cell), and thrombocytopenia (few platelets in blood) can also occur and be dose limiting. Also, some patients are unable to continue using Bortezomib due to its toxicity. Clinically, multiple myeloma patients typically cannot be dose escalated beyond a certain dose (for example, 1-2 mg/meter square) using Bortezomib until a satisfactory response is achieved because of intolerable side effects. Further, 20-60% of patients previously treated by other agents, as well as around 10% of first-time patients, do not respond to proteasome inhibition therapy (e.g., Bortezomib). Patients that do respond to Bortezomib may eventually become resistant to the treatment.

Bortezomib may cause increased immunoglobulin production by plasma cells that exceeds the protein folding capacity of the endoplasmic reticulum (ER). This may result in the accumulation of aberrant proteins that triggers an unfolded protein response (UPR). As aberrant proteins within the ER further accumulate, they may ultimately cause apoptosis. However, Bortezomib is often times clinically ineffective in causing apoptosis in MM cells.

The inventors of the present invention discovered that one possible mechanism, though relied upon and presented herein only as a non-limiting explanation, is presented in FIG. 1. The proteasome inhibitors may be ineffective because the proteasome inhibitors may trigger an unfolded protein response in the cell, which may in turn trigger Hsp upregulation, including the chaperone Hsp70 and also Hsp90. Thus, the cell can survive while it is under stress.

The inventors of the present invention focused research on the effects of Hsp70 as a chaperone to multiple myeloma cells, as well as determining Hsp70 inhibitors. One Hsp70 inhibitor synthesized and characterized by the inventors, MAL3-101, has been found to have potent affects on various multiple myeloma cell lines, when used individually and in combination with a proteasome inhibitor (e.g. MG-132) and an Hsp90 inhibitor (e.g. 17-AAG). Thus, one or more derivatives of MAL3-101 present a new class of compounds which are effective cancer therapies, and Hsp70 inhibitors. MAL3-101 is a member of the class of dihydropyrimidinone peptoids, and is a potent and effective small molecule inhibitor of Hsp70. MAL3-101, as well as other dihydropyrimidinones are effective Hsp70 inhibitors, and present a potent therapy and/or treatment against both tumors and their microvasculature, which is responsible for feeding and supporting tumor growth.

Therefore, new methods and new agents that themselves block MM cell growth or that potentiate the effect of existing treatments for MM are provided with the embodiments of the present invention. Although proteasome inhibitors (e.g., MG-132 in the lab and Bortezomib in the clinic) do indeed inhibit MM cell growth, drug resistance, long term toxicity, and serious negative side effects have thwarted the efficiency and effectiveness of the treatment. However, the inventors have determined that MAL3-101 (and derivatives there of) may potentiate the antimyeloma effects of proteasome inhibitor MG-132 which may benefit both newly diagnosed as well as relapsed multiple myeloma patients. By increasing the effectiveness of MG-132, even partial simultaneous inhibition of Hsp70 may overcome resistance to proteasome inhibitors seen in certain patients, and may help provide a more durable response in all patients to anti-oncogenic therapies and treatments.

Further, the inventors have discovered that by using dihydropyrimidinone compounds exhibiting Hsp70 inhibitor characteristics in combination with proteasome inhibitor MG-132, lower amounts of each compound may be used in order to effectively treat the multiple myeloma cells. Specifically, a synergistic apoptotic effect results, in which a small amount of each of the inhibitors used, in combination, provides a benefit greater than their additive effect. Thus, small amounts of MAL3-101 and MG-132 provide a synergy of treatment which results in the effective treatment of multiple myeloma cells in which large percentages of cancerous cells undergo apoptosis in a relatively short time course after only a single treatment. As the concentration of amounts of the inhibitors is small, toxic effects are minimized, while apoptosis of cancerous cells is maximized. Thus, Hsp70 inhibitors, including those from but not limited to the dihydropyrimidinone class, may potentiate the effects of proteasome inhibitors to provide an effective treatment for Hsp70 dependent cancers, like multiple myeloma. As such, Hsp70 inhibitors may be used to overcome cell resistance to proteasome inhibitors and avoid neurotoxicity and gastrointestinal side effects (diarrhea, nausea, vomiting, and low appetite) that may limit the use of proteasome inhibitors or other treatments. By potentiating or facilitating the effect of proteasome inhibitors, Hsp70 antagonism allows the use of smaller doses of proteasome inhibitors to achieve stronger effects. Addition of Hsp70 inhibitors to combination regimens that include proteasome inhibition or Hsp90 inhibitors and/or other forms of anti-oncogenic therapies would also be beneficial by overcoming resistance and also by allowing dose reduction.

Though there are several types of Hsp modulators, including RNAi and antisense, MAL3-101 represents a new class of small molecule compound. There exists a continued need for small molecule compounds which may be effectively co-administered with other treatments, exhibit high bioactivity, and exhibit a high solubility in the body in order to effectively treat a plurality of Hsp70 dependent cancer cells. Thus, the inventors provide a class of dihydropyrimidinone peptoid inhibitors which may meet or exceed the characteristics of MAL3-101, including having even smaller molecular weights, higher bioactivity, and higher solubility than MAL3-101.

It may also be desirable to change the scope of the MAL3-101 or derivative compound, in order to, for example, increase the yield of product, increase solubility in various solvents, modify the affects or potency of one or more characteristics of the compound, affect efficiency of production or manufacture, or alter one or more negative side effects of the compound in its use. Given the fact that MAL3-101 derivatives may be a potentially promising candidate in overcoming drug resistance to proteasome inhibitors and effectively treating Hsp-dependent cancers like multiple myeloma, exploring the characteristics of derivatives and their potential role as Hsp inhibitors may be important to increasing the effectiveness of the Hsp70 inhibitor relative to the overall chaperoning mechanism. As such, the compound, MAL3-101 may be modified to a derivative form, similar in one or more essential characteristics of its original structure and function by incorporating one or more various functional groups or replacing current functional groups with other groups.

Figure 2:
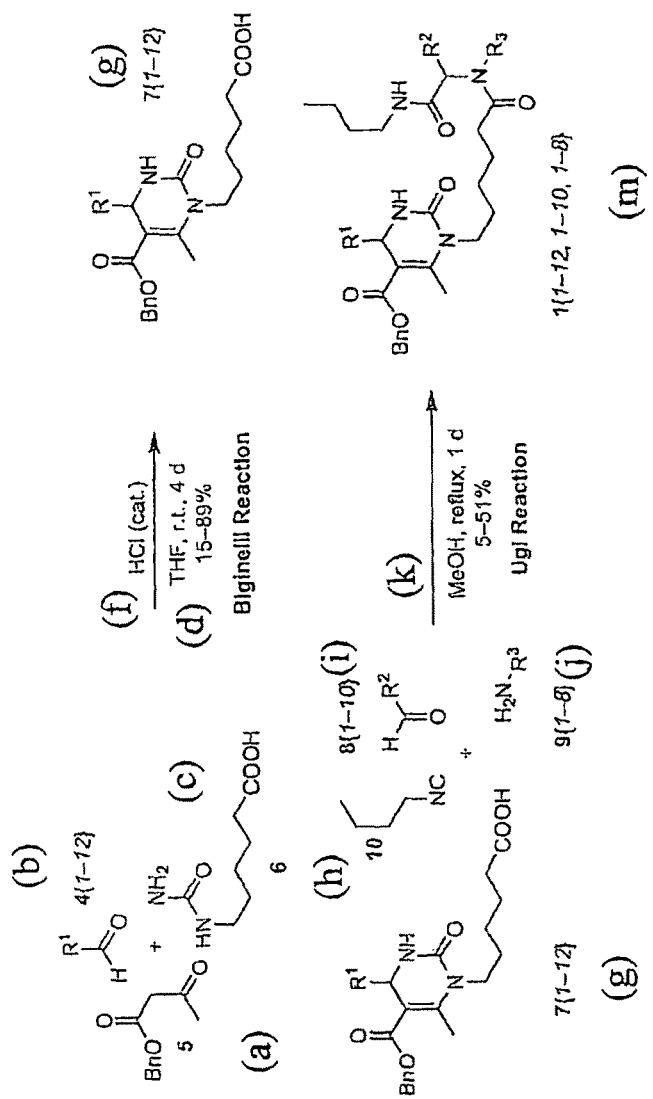
FIG. 2 depicts a mechanism for the chemical synthesis of compounds which may have Hsp70 inhibiting effects.
Figure 3:
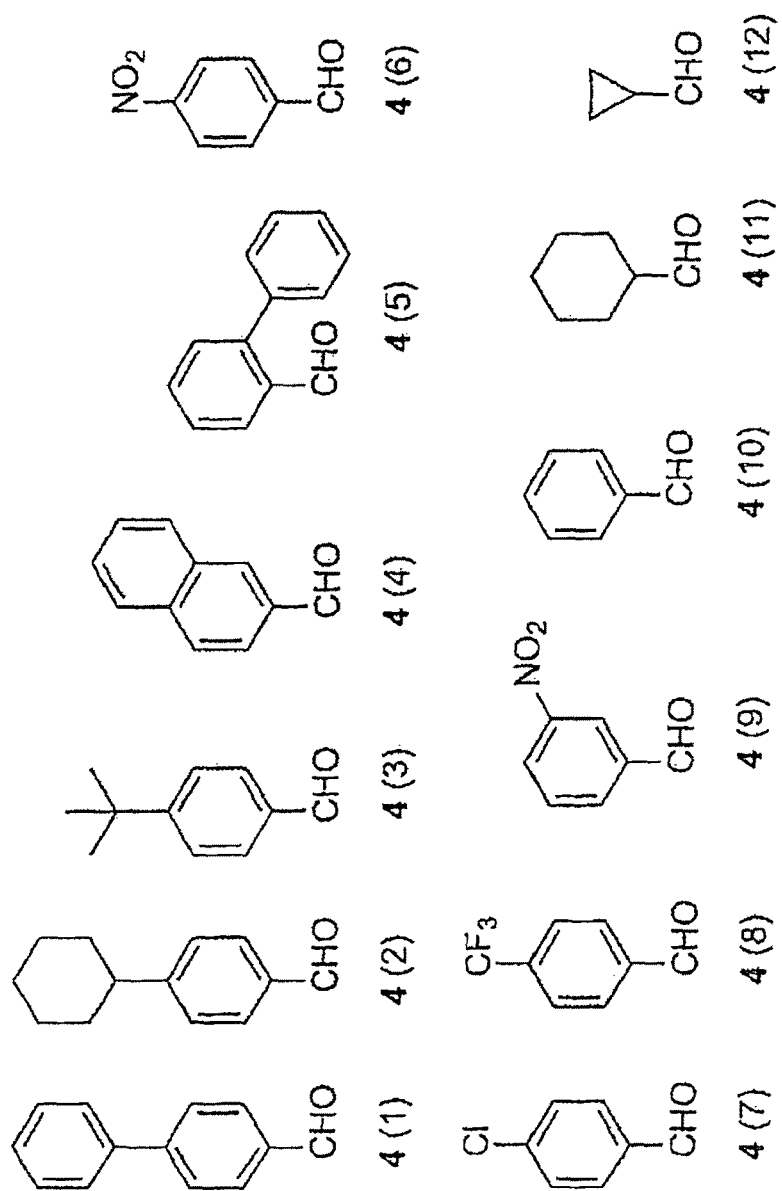
FIG. 3 depicts various functional groups that may be substituted onto one of the compounds disclosed in the Biginelli synthesis related to an example of compounds that may have Hsp70 inhibiting effects.
Figure 4:
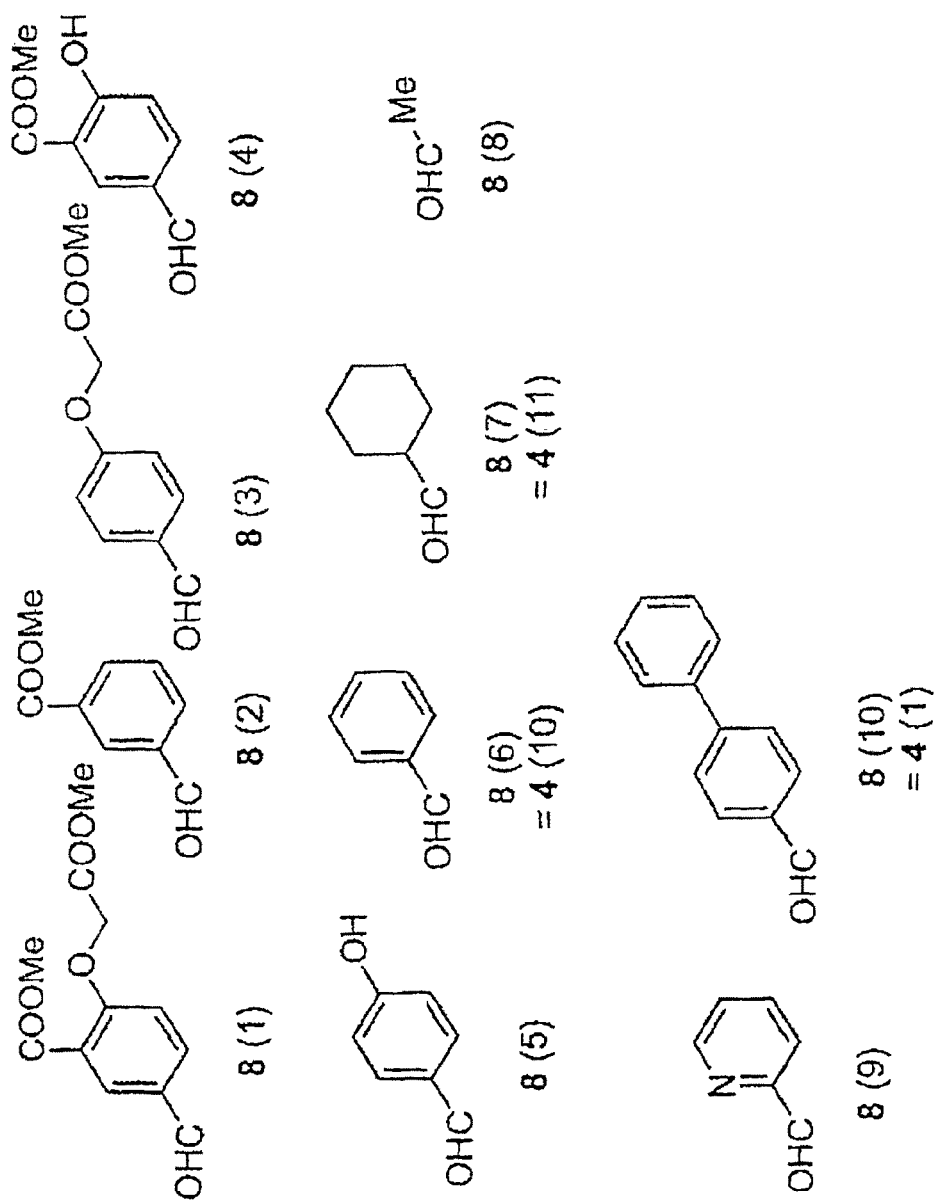
FIG. 4 depicts various functional groups that may be substituted onto one of the compounds disclosed in the Biginelli synthesis in order to synthesize compounds which may have Hsp70 inhibiting effects.
Figure 5:
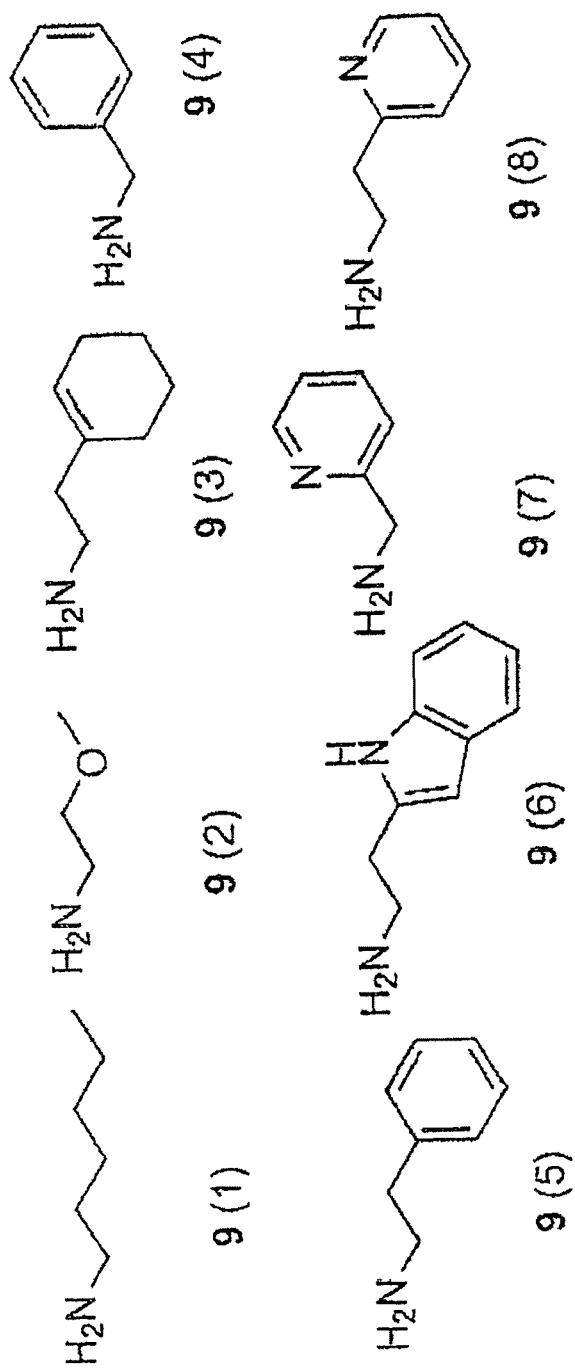
FIG. 5 depicts various functional groups that may be substituted onto one of the compounds disclosed in the Ugi synthesis in order to synthesize compounds which may have Hsp70 inhibiting effects.
Figure 6:
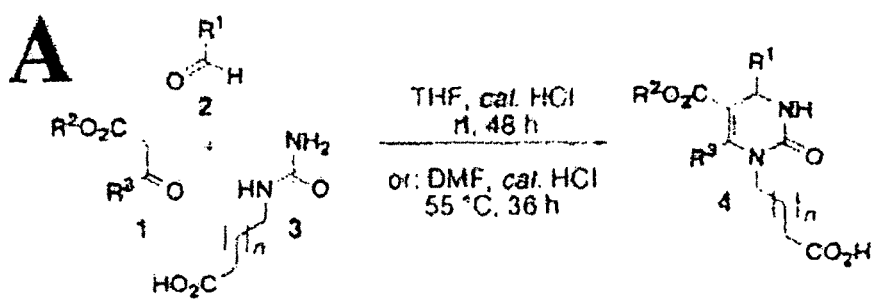
FIG. 6 depicts an example of an alternative precursor Biginelli synthesis which may be used in order to synthesize compounds which may have Hsp70 inhibiting effects.
Figure 7:
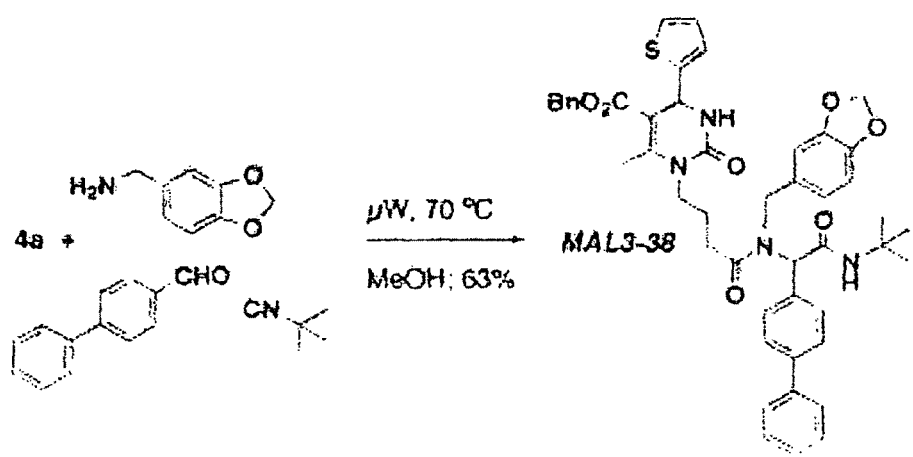
FIG. 7 depicts an example of an alternative Ugi synthesis which may be used in order to synthesize compounds which may have Hsp70 inhibiting effects.
Figure 8:
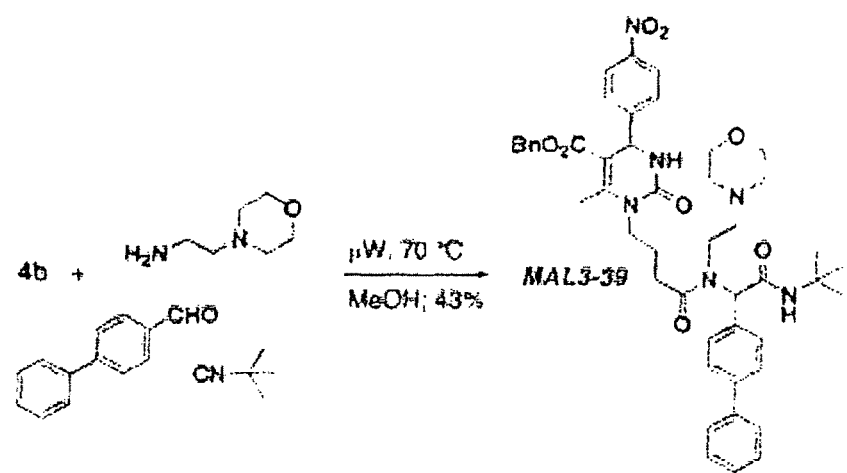
FIG. 8 depicts another example of an alternative Ugi synthesis which may be used in order to synthesize compounds which may have Hsp70 inhibiting effects.
Figure 9:
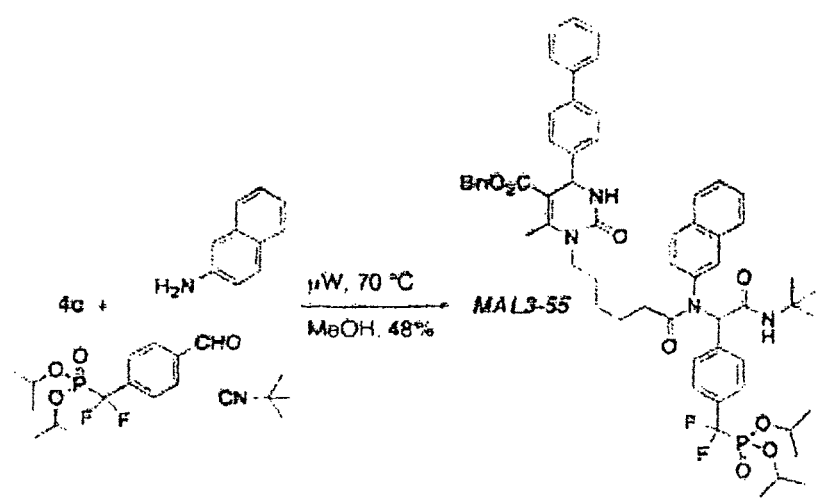
FIG. 9 depicts still another example of an alternative Ugi synthesis which may be used in order to synthesize compounds which may have Hsp70 inhibiting effects.
Figure 10:
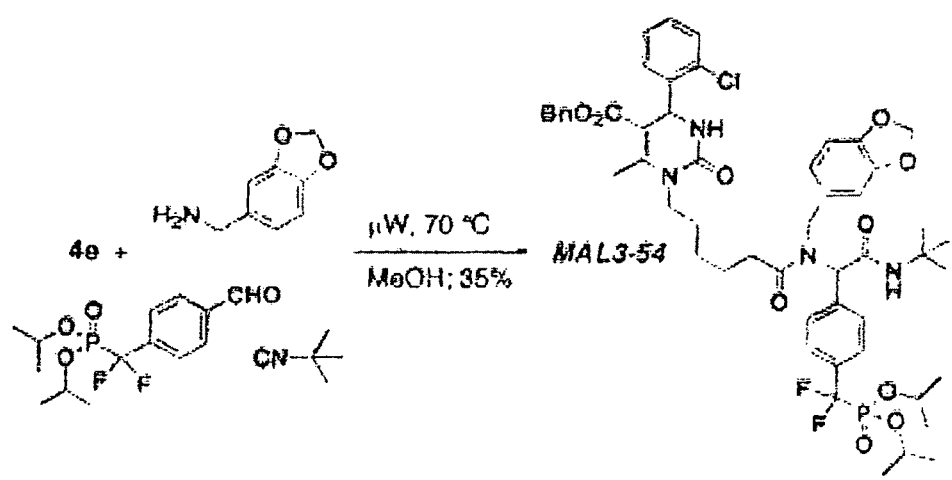
FIG. 10 depicts still yet another example of an alternative Ugi synthesis which may be used in order to synthesize compounds which may have Hsp70 inhibiting effects.
Figure 11:
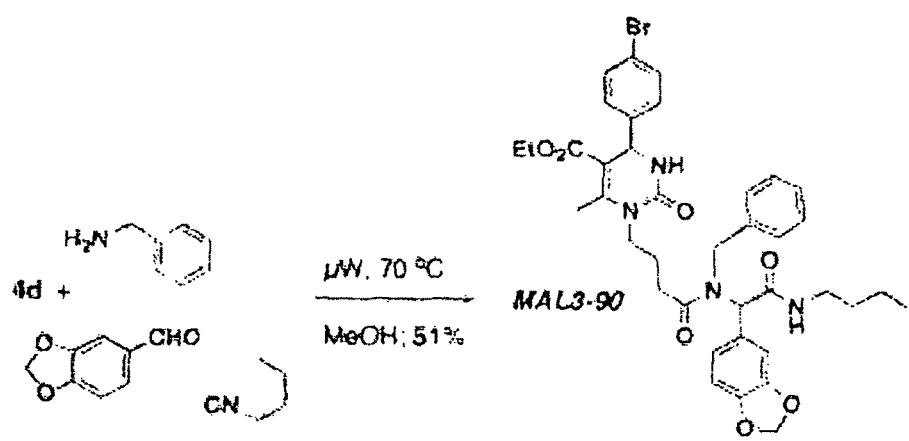
FIG. 11 depicts still further another example of an alternative Ugi which may be used in order to synthesize compounds which may have Hsp70 inhibiting effects.
Figure 12:
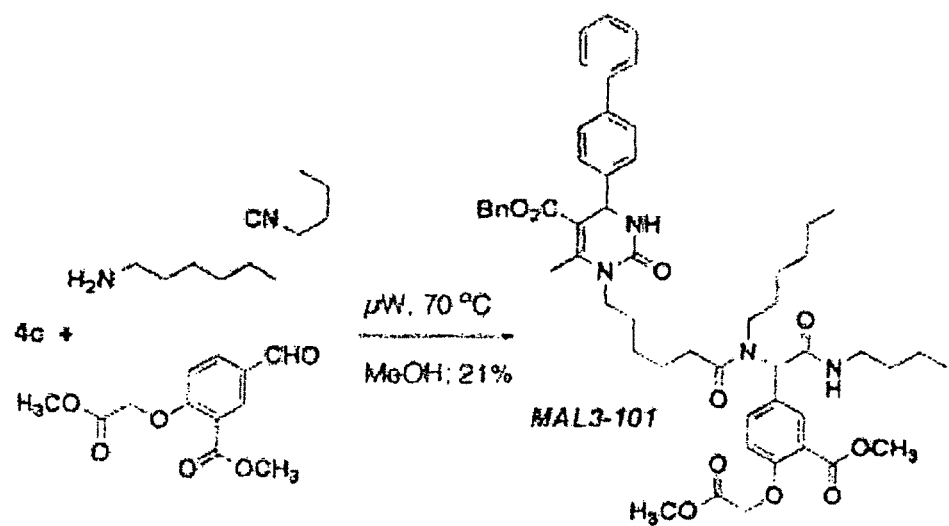
FIG. 12 depicts further still another example of an alternative Ugi synthesis related to one Hsp70 inhibitor, MAL3-101.
Figure 13:
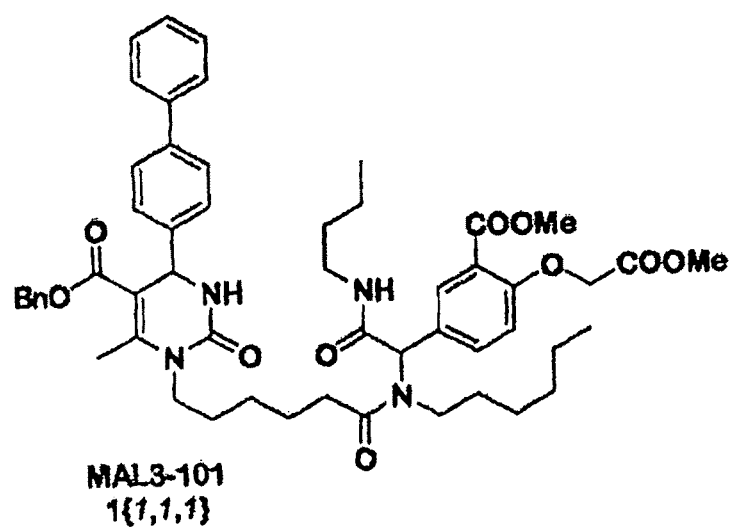
FIG. 13 is a representative chemical depiction of one Hsp70 inhibitor, MAL3-101.

The generic molecule, as shown below as the end product in FIG. 2 and referred to as pyrimidinone or pyrimidinone-peptoid, may be amended to various forms, as may be desired, in order to achieve such a goal. The various reaction sequences, various substituting groups (R groups), intermediates, and final products may be referred to herein may be depicted in a clear and articulate manner in FIG. 2 through FIG. 13 and described in the examples section. As it provides additional discussion of the synthesis and characterization of MAL3-101 and MAL3 derivative compounds, the publication: S. W. Fewell, C. M. Smith, M. A. Lyon, T. P. Dumitrescu, P. Wipf, B. W. Day, J. L. Brodsky, Small molecule modulators of endogenous and co-chaperone-stimulated Hsp70 ATPase activity, J Biol Chem 279 (2004) 51131-51140 is incorporated by reference herein in its entirety. Also, the publication C. M. Wright, R. J. Chovatiya, N. E. Jameson, D. M. Turner, G. Zhu, S. Werner, D. M. Huryn, J. M. Pipas, B. W. Day, P. Wipf, and J. Brodsky, Pyrimidinone-peptoid hybrid molecules with distinct effects on molecular chaperone function and cell proliferation, Bioorganic & Medicinal Chemistry 16 (2008) 3291-3301 details the synthesis of MAL3-101 derivatives that may be effective as Hsp70 inhibitors, and is thus, incorporated by reference herein in its entirety, with various syntheses descriptions provided in the experimental data section.

The products referenced therein, as well as the examples section, may also include their tautaunomers, enantiomers, stereoisomers, racemates, etc. Also, one or more of the representative figures may not accurately depict steric orientation of one or more of the molecules. Although a synthesis is provided in the examples section, it is noted that the disclosure is merely an exemplary, non-limiting disclosure, and there may be one or more methods, procedures, and syntheses available in varying steps to yield the same, or substantially similar, compound. Although members of the MAL3 class of compounds, as well as various derivatives of MAL3-101, are provided and included in the disclosure of the present invention, specifically, the MAL3-101 compound may be referenced herein in a non-limiting, exemplary manner.

Disclosed inter alia, various embodiments of the present invention deal with treatment of cancer cells and tumors as well as live tissue applications. As a preliminary matter, the materials and methods will be outlined, and respective data highlighted relevant to the present invention. As discussed below, various cell lines, primary cell cultures, and biological samples may be utilized in practicing examples of one or more of the various embodiments of the present invention.

Figure 14:
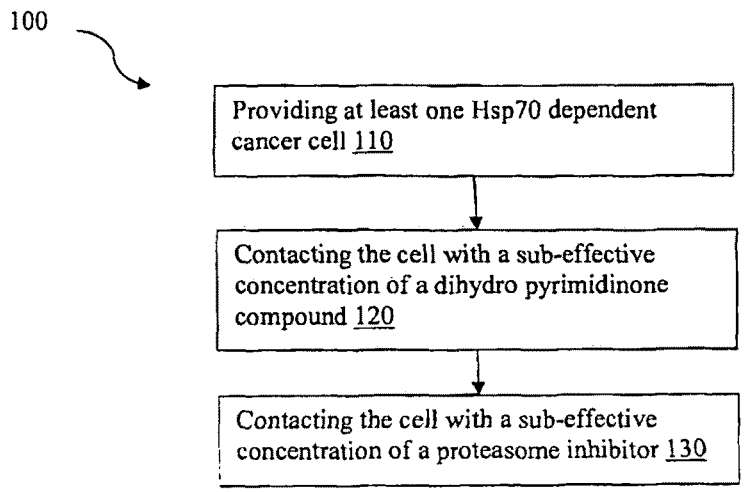
FIG. 14 is a flow chart depicting an embodiment of a method of treating an Hsp70 dependent cancer.
Figure 15:
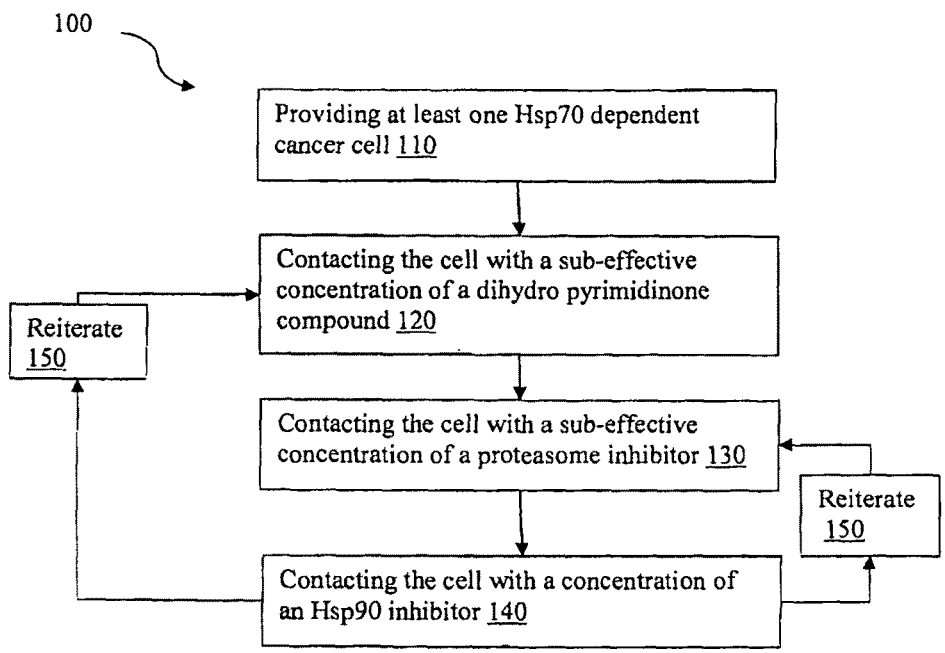
FIG. 15 is a flow chart depicting another embodiment of a method for treating an Hsp70 dependent cancer.

With reference to FIGS. 14 and 15, flowcharts for an embodiment a method of treating an Hsp70 dependent cancer are provided. The method 100 of treating an Hsp70 dependent cancer, may include the steps of: providing 110 at least one Hsp70 dependent cancer cell; contacting 120 the at least one cell with a sub-effective concentration of a dihydro pyrimidinone compound; and contacting 130 the at least one cell with a sub-effective concentration of a proteasome inhibitor, wherein the sub-effective concentration of the dihydropyrimidinone compound and the sub-effective concentration of the proteasome inhibitor have a synergistic effect upon the at least one cell. Optionally, the method 100 may further include the step of contacting 140 the cell with a concentration of an Hsp90 inhibitor. One of more of the steps of the method 100 may be repeated, or reiterated 150, as may be desired in order to effectuate a desired result or treatment regimen.

Figure 16:
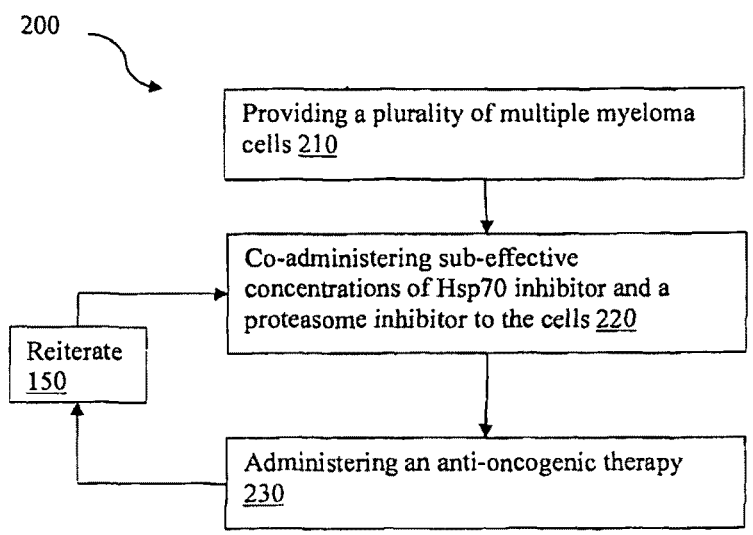
FIG. 16 is a flow chart depicting an embodiment of a method for treating multiple myeloma.

With reference to FIG. 16, a method 200 of treating multiple myeloma is provided. The method 200 of treating multiple myeloma may include the steps of: providing 210 a plurality of multiple myeloma cells, co-administering 220 a sub-effective concentration of each of a Hsp70 inhibitor and a proteasome inhibitor to the plurality of cells, wherein the sub-effective concentrations of the Hsp70 inhibitor and the proteasome inhibitor together have a synergistic apoptotic effect on the multiple myeloma cells. Optionally, the method 200 may further include the step of administering 230 an anti-oncogenic therapy along with the co-administration of the Hsp70 inhibitor and the proteasome inhibitor. The anti-oncogenic therapy may be one or more cancer therapies, including chemotherapy, surgery, hormone therapy, radiation therapy, and other types of therapies and treatments, as may be desired.

Figure 17:
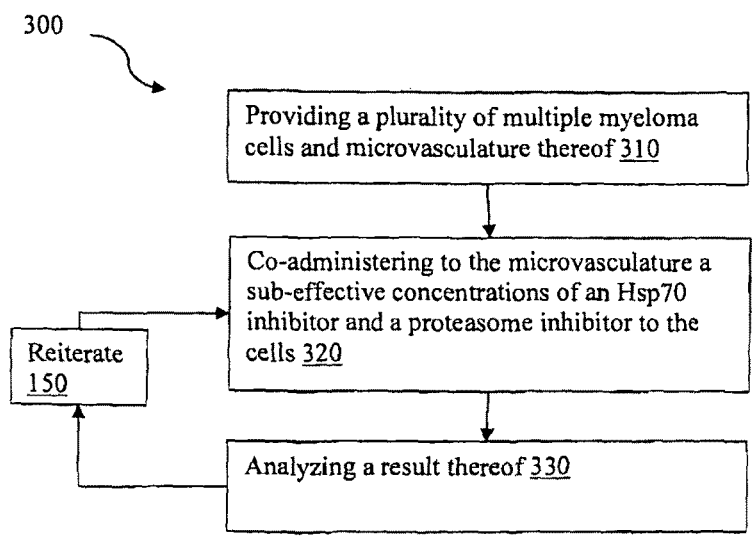
FIG. 17 is a flow chart depicting another embodiment of a method for treating multiple myeloma by treating the microvasculature thereof.

With reference to FIG. 17, the method 300 of treating multiple myeloma is provided. The method 300 of treating multiple myeloma includes the steps of: co-administering 320 to a microvasculature of a plurality of multiple myeloma cells a sub-effective concentration of an Hsp70 inhibitor and a sub-effective concentration of a proteasome inhibitor, wherein the Hsp70 inhibitor and the proteasome inhibitor have a synergistic effect on the microvasculature. After the co-administration step 320, the method 300 may optionally include the step of analyzing 330 a result thereof. By treating the microvasculature which surrounds and supports the multiple myeloma cells, including tumors, the method effectively treats multiple myeloma. That is, the treatment effectively targets endothelial progenitor cells which feed the multiple myeloma cells, so that once the endothelial progenitor cells are killed, the multiple myeloma cells will also die, of necrosis by lack of nutrients and oxygen, if not apoptosis by the Hsp70 inhibitor and proteasome inhibitor. The analysis step 330 may include one or more types of analysis and/or determination of the effectiveness of the treatment, clinical information on the multiple myeloma, etc. Optionally, one or more steps may be repeated or reiterated 150 until a desired effect or result is reached.

Figure 18:
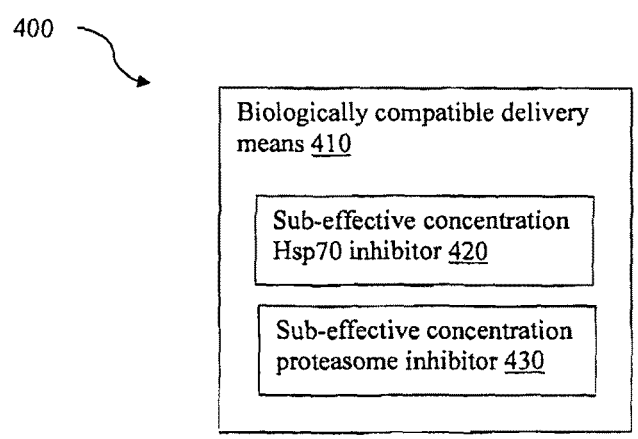
FIG. 18 is a block diagram depicting an embodiment of a combination therapy for a plurality of Hsp70 dependent cancer cells.

With reference to FIG. 18, a combination therapy 400 is provided. The combination therapy may be used to treat one or more types of Hsp70 dependent cancer, including multiple myeloma. The combination therapy 400 for a plurality of Hsp70 dependent cancer cells may include: a sub-effective concentration of an Hsp70 inhibitor 420; a sub-effective concentration of a proteasome inhibitor 430; and a biologically compatible delivery means 410. The biologically compatible delivery means 410 may include one or more types of solvents or diluents which may suspend or solubilize the medicaments (the Hsp70 inhibitor and proteasome inhibitor) such that the medicaments may be absorbed into the plurality of cells for treatment. One such biologically compatible delivery means 410 includes dimethyl sulfoxide (DMSO), which may be contacted to a culture of cells or administered topically onto a plurality of cells, as with tumor treatment or with a large volume of cells to be treated.

Figure 19:
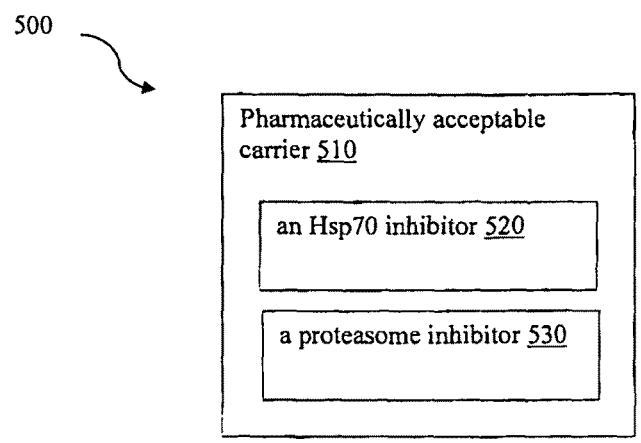
FIG. 19 is a block diagram depicting an embodiment of a composition of matter for a plurality of Hsp70 dependent cancer cells.

With reference to FIG. 19, a composition of matter 500 useful in the treatment of Hsp70 dependent cancers is provided. The composition of matter 500 may be used to treat various forms of Hsp70 dependent cancer, including multiple myeloma. The composition of matter 500 may include: an Hsp70 inhibitor 520; and a proteasome inhibitor 530, where each of the Hsp70 inhibitor 520 and the proteasome inhibitor 530 may be in a pharmaceutically acceptable carrier 510. As the Hsp70 inhibitor 520 and the proteasome inhibitor 520 are held within the pharmaceutically acceptable carrier 510, the carrier 510 and inhibitors 520, 530 are together administrable to a plurality of Hsp70 dependent cancer cells. For its administration into a plurality of cells, some of which are multiple myeloma cells, the Hsp70 inhibitor and the proteasome inhibitor may be in a pharmaceutical composition including a pharmaceutically acceptable carrier in order to travel through the cells, or tissue to the site of one or more multiple myeloma cells. The Hsp70 inhibitor, the Hsp90 inhibitor (if used) and the proteasome inhibitor may take the form of, for example, a metabolite, paramorph, or a pharmaceutically acceptable salt thereof so that the components may be solubilized and in bioactive form. Pharmaceutically acceptable delivery methods include characteristics such that the therapeutic effect are maximized, the Hsp70 inhibitor and/or proteasome inhibitor states may be optimal for delivery in vitro into a tissue sample, or possibly in vivo to the desired location within a living organism, and other variables of treatment may be optimized and made more efficient.

The composition of matter may take one or more forms, as may be desired. Preferably, the composition of matter may be of the various inhibitors suspended in DMSO, for a subject to drink or for administration directly on or to a sample of cells to be treated. It should be noted that the composition of matter may also be a swallowable pill, an inhalable powder, a suppository, an imbibed liquid, a transdermal application, or an injectable component, or a surgically implantable material. It is understood that these carriers listed as examples are non-limiting and other carriers may also be contemplated. Inert materials include materials, which increase the weight and volume of the composition, but themselves have no effects at all in relation to the administration of the composition of matter. Inert materials may comprise fillers, binders, disintegrants, lubricants, colorants, or flavorants. Still other materials may be added to the composition of matter, for example, to increase solubility or delivery of the composition to the plurality of cells.

Figure 20:
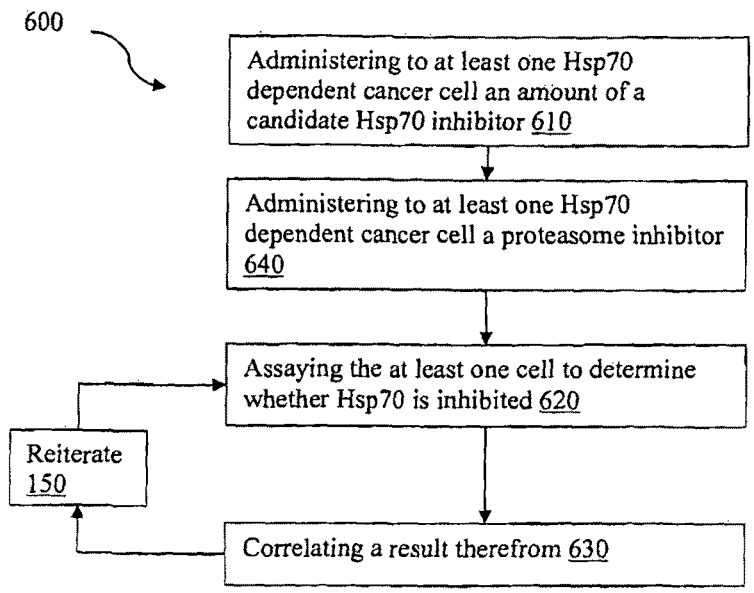
FIG. 20 is a flowchart depicting an embodiment of a method of screening candidate Hsp70 inhibitors.

FIG. 20 provides a flowchart depicting a method 600 of screening Hsp70 inhibitors. The method 600 may include the steps of: administering 610 to at least one Hsp70 dependent cancer cell an amount of a candidate Hsp70 inhibitor; and assaying 620 the at least one cell to determine whether Hsp70 is inhibited. Optionally, as is shown in FIG. 20, the method may further include the step of administering 640 to at least one Hsp70 dependent cancer cell a proteasome inhibitor. After the assaying 620 step, the method 600 may further include the step of correlating 630 at least one result. The step of correlating 630 a result may include completing various analyses and comparing it to that of, for example MAL3-101, a compound that is a known Hsp70 inhibitor which is effective in individual or combination treatment of Hsp-dependent cancer. Further, various experimental data may be performed with MM cell lines, in order to determine, for example, whether certain forms of multiple myeloma are better treated with one form or another of candidate Hsp70 inhibitors. Such assays and experimentation may be further detailed in the Examples section. Also, one of more of the steps may be reiterated 150 or repeated, as may be desired.

Figure 21:
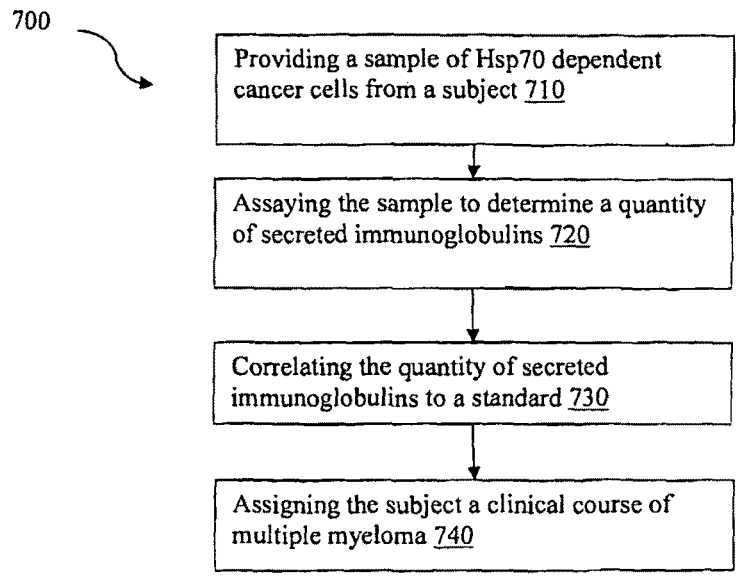
FIG. 21 is a flowchart depicting an embodiment of a method of diagnosing a progression of Hsp70 dependent cancer.

With reference to FIG. 21, a method 700 of diagnosing a progression of Hsp70 cancer is provided. The method 700 may include the steps of: providing 710 a sample of Hsp70 dependent cancer cells from a subject; assaying 720 the sample to determine a quantity of secreted immunoglobulins; correlating the quantity of secreted immunoglobulins to a standard 730. The standard may include any reference tool used or relied upon by clinicians and/or medical professionals in order to gauge the effectiveness of a treatment. Alternatively, the standard may be a table or reference, including printed publications, which may refer to various levels of assays in order to reference them to a level or aggressiveness of a multiple myeloma course of treatment. Optionally, the method may further include the step of assigning 740 the subject a clinical course of multiple myeloma. The clinical course of multiple myeloma may refer to the clinical prognosis of the disease, likely life expectancy, aggressiveness of the disease, and/or types of therapies or treatments that may be preferably performed to accord to the level of disease in a subject. This clinical course may detail, for example, the expected survival of the patient, the relative size of a tumor or progression of MM cells, the preferred courses of treatment, and the like as may be desired.

Figure 22:
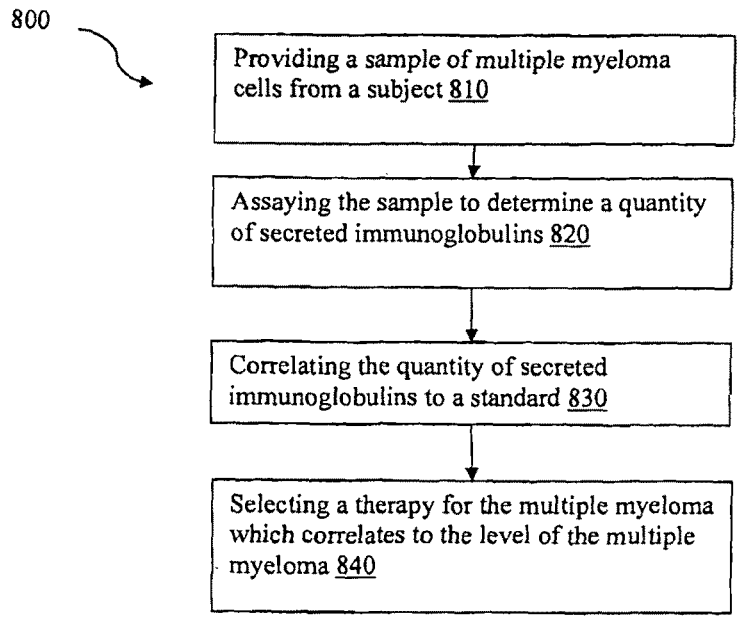
FIG. 22 is a flowchart depicting an embodiment of a method of determining a therapy for a multiple myeloma patient in need thereof.

With reference to FIG. 22, a method 800 for determining a therapy for a multiple myeloma patient in need thereof is provided. The method 800 may include the steps of: providing 810 a sample of multiple myeloma cells from a subject; assaying 820 the sample to determine a quantity of secreted immunoglobulins; and correlating 830 the quantity of secreted immunoglobulins to a standard; wherein each quantity is assigned to a level of multiple myeloma, wherein a high level correlates to an aggressive multiple myeloma, while a low level correlates to a less aggressive multiple myeloma. Optionally, the method 800 may further include the step of selecting 840 a therapy for the multiple myeloma which correlates to the level of multiple myeloma. A conservative treatment or combination therapy may be selected for a patient that is correlated to have a less aggressive myeloma. Thus, the patient may be prone to survive longer, be more responsive to lower concentration levels of treatments, shorter treatment cycles, and the like. A more aggressive treatment may likewise be chosen for a more aggressive myeloma. In such a manner, more aggressive therapies, combination therapies (including for example, synergistic inhibitor therapies and/or chemotherapy, surgery, etc.), and higher concentrations or longer duration treatments may be administered to a patient with a more aggressive myeloma.

With reference to the methods 100, 200, 300, 600, 700, 800, the combination therapy 400, and the composition of matter 500, the Hsp dependent cancer cell may refer to a type of cancer that is adversely affected by Hsp70 inhibitors, including for example, Hsp70 dependent cancer.

Hsp70 dependent cancers treated with Hsp70 inhibitors, including, for example, MAL3-101, may show apoptosis, may cease in growth, or may provide other benefits in treatment. For example, Hsp70 dependent cancer may be more susceptible to other forms of cancer treatments and therapies after Hsp70 inhibitor treatment, including for example, proteasome inhibitor, Hsp90 inhibitors, or other known anti-oncogenics, including radiation therapy, chemotherapy, surgery, and/or hormone therapy. The Hsp70-dependent cancer cell may be at least one multiple myeloma cell, a breast cancer cell, or a melanoma cell or other cancers which may rely on an exhibition of Hsp70 upregulation in order to prevent apoptosis, necrosis, or other cell harm. Alternatively, the Hsp-dependent cancer cell may be an Hsp90 dependent cancer cell, including, for example, small cell lung carcinoma, which may benefit from Hsp70 inhibitor, Hsp90 inhibitor, and proteasome inhibitor treatments.

The at least one Hsp70 dependent cancer cell referred to in the methods 100, 200, 300, 600, 700, 800, the combination therapy 400, and the composition of matter 500, may refer to one Hsp70 dependent cancer cell or a plurality of cells. The plurality of cells may be obtained from a subject diagnosed with one or more forms of Hsp or Hsp70 dependent cancer. The plurality of cells may be a cancer site, a metastasized tumor, or a combination of cancerous and non-cancerous cells/tissue in or from a subject. The subject may be a mammal, and specifically, may comprise a living organism, a laboratory research animal, or mammals including rats, guinea pigs, cats, pigs, monkeys, and/or humans. Also, the plurality of cells may be a biological sample taken from a patient currently exhibiting symptoms of such a cancer, where the patient has not yet been diagnosed, or may be in relapse of an Hsp dependent cancer. The plurality of cells may also be from cultured cells, or from a commercially available cell line (as from a medical supplier). The at least one cell may comprise one cell, a plurality of cells, or a colony of cancer cells, as is such with a tumor. Further, the plurality of cancer cells may be included in a quantity of cells that may contain one or more healthy normal cells. The plurality of cells may further include the surrounding microvasculature of the Hsp70 dependent cancer cells, for example, the endothelial progenitor cells.

Administration, as may be referred to in the methods 100, 200, 300, 600, 700, 800, the combination therapy 400, and the composition of matter 500, may refer to contacting or otherwise placing the various inhibitors within range of the cells in order to effectuate one or more therapeutic affects thereon. For example, the Hsp70 inhibitor, the Hsp90 inhibitor, and/or the proteasome inhibitors, may be contacted to the cells or desired site of contact for treatment as by topical administration or absorption with, for example, a solution, a biologically acceptable means of delivery, or a pharmaceutically acceptable delivery means. The administration step may refer to the application of one or more of the inhibitors or candidate inhibitors to effectuate one or more of the methods to the one or more Hsp70 dependent cancer cells, or multiple myeloma cells. Co-administration may refer to administering, for example, an Hsp70 inhibitor with a proteasome inhibitor and/or an Hsp90 inhibitor to one or more cells, as described, at substantially the same time, or subsequent to one another. One or more inhibitors may be administered at a predetermined time, such that one inhibitor may be administered seconds, minutes, hours, days, weeks, or months apart from the other inhibitor, for example, pursuant to a prescribed plan or treatment schedule. Further, in the case where co-administration to a plurality of cells, including a tumor or large tissue sample, the co-administration at substantially the same time, need not be either in the same location on the cells or be in the same biologically active or pharmaceutically acceptable delivery means. Co-administration may refer to administering both an Hsp70 inhibitor and a proteasome inhibitor in the same treatment cycle, though not with contiguous timing of administration. By treatment cycle, it is understood to mean that one or more administrations of the proteasome inhibitor or the Hsp70 inhibitor may be given over a predetermined period of time, or pursuant to symptoms of the subject or toxicity tests, assays or analyses of cell samples, or other screenings to gauge effectiveness. Contacting, as used herein, may refer to a type of administration. The step of contacting may refer to, for example, administering or contacting a candidate inhibitor or inhibitor in an acceptable solution, mixture, or liquid form such that the solution comes into effective proximity with one or more of the at least one Hsp70-dependent cancer cell.

Similarly, the present invention may further be used to test candidate proteasome inhibitors and/or candidate Hsp90 inhibitors which may be used individually or in combination therapies in order to treat Hsp dependent cancers. The method for testing candidate proteasome inhibitors may include the steps of: providing at least one Hsp70-dependent cancer cell; contacting to at least one cell an amount of a candidate proteasome inhibitor; contacting the Hsp70-dependent cancer cell with an amount of an Hsp70 inhibitor; analyzing the at least one Hsp70-dependent cancer cell; and quantifying at least one result. Once the at least one Hsp70-dependent cancer cell is contacted with a candidate proteasome inhibitor, the at least one Hsp70-dependent cancer cell may have an apoptotic effect upon the cells, or alternatively chaperone the cells by upregulating Hsp70 and/or Hsp90, which is characteristic, as with Bortezomib (or MG-132) that the cell is under stress and is upregulating heat shock proteins in order to avoid apoptosis. Such upregulation of Hsps may be measured or assayed, as may be desired. Subsequently, the treatment may further include administering or co-administering to the cells one or more Hsp70 inhibitor and/or Hsp90 inhibitor.

The proteasome inhibitor used with one or more of the methods 100, 200, 300, 600, 700, 800, the combination therapy 400, and the composition of matter 500 may be MG-132, or clinically, Bortezomib. The Hsp70 inhibitor used with one or more of the methods 100, 200, 300, 600, 700, 800, the combination therapy 400, and the composition of matter 500 may be a member of the dihydropyrimidinone peptoid class of compounds, the dihydropyrimidinone class of compounds, MAL3-101, and/or a derivative of MAL3-101. An example of an Hsp90 inhibitor may include, geldanamycin (GA) or 17-allylamino-17-demethoxy-geldanamucin (hereinafter referred to as 17-AAG). The Hsp90 inhibitor 17-AAG, an active analogue of GA, may be available from a medical provider, such as Calbiochem/EMD Biosciences in Germany. The Hsp90 inhibitor 17-AAG may be administered in delivery methods previously disclosed for the proteasome inhibitor and Hsp70 inhibitor. The Hsp70 inhibitor may be administered individually or in combination with one or both of an Hsp90 inhibitor (for example, 17-AAG) and a proteasome inhibitor (for example, MG-132). Methods of administration were previously discussed, and include cellular contact as well as topical administration, as to a tumor or living tissue sample. The Hsp70 inhibitor used with the methods, composition of matter, and combination therapy of the present invention may be characterized in that they may exhibit small molecular weights, high bioactivity/bioavailability, and high solubility in one or more biologically acceptable delivery means.

Delivery of the proteasome inhibitor, the Hsp70 inhibitor, and/or the Hsp90 inhibitor to the at least one Hsp70 dependent cancer cells may be effectuated by intravenous administration, inhalation administration, insulfation administration, imbibition administration, consumption administration, transdermal administration, surgical implantation administration, and combinations thereof.

The Hsp70 inhibitor may further comprise a MAL compound, or a derivative thereof. The various characteristics of the MAL compound class as Hsp70 inhibitors may provide an Hsp70 inhibitor that has the inhibiting properties of, for example, MAL3-101, or greater effects thereof. The MAL class of compounds may include, for example, those discussed in the examples section as a product of Biginelli and Ugi Syntheses depicted in FIG. 2 through FIG. 13. Specifically, this may include the compounds depicted as end products of the Biginelli-Ugi synthesis, referenced in FIG. 2 through FIG. 12. These compounds may be referred to as MAL compounds or derivatives. MAL3-101 may be depicted in FIG. 13.

One or more of the methods 100, 200, 300, 600, 700, 800, the combination therapy 400, and the composition of matter 500 may further include the step of analyzing at least one Hsp70-dependent cancer cell. Analysis may include one or more methods, as may be desired, in order to determine, through accepted laboratory procedures, microscopic assay, and observation techniques variables of information pertaining to the administration of treatment to the at least one cell and resulting cellular response to the treatment. For example, the at least one Hsp70-dependent cancer cell may be analyzed by microscopic examination. Assays performed as part of the analysis may include, for example, MTS assay (computation of survival assay), ELISA (calorimetric analysis indicative of mitochondrial damage), and actual apoptosis (immunofluorescent technique) to determine cell death and necrosis. Additional discussion is provided in the Examples section. Analysis of larger tissue samples, or possibly an in vivo treatment may comprise taking one or more biological data sample(s) from a subject and performing one or more of the previously discussed assays. Also, analysis in vivo may comprise observing a living subject for side effects or other characteristics affects of Hsp70 inhibitors and proteasome inhibitors within the body.

For example, multiple myeloma cell lines and primary patient multiple myeloma cells may be examined. Dose-response and time-course studies may comprise one or more components of the analysis. For example, the method may be completed on multiple myeloma cell lines U266, RPM1-8226, and NCI-H929. Through the analysis, the at least one result may be that the cells showed an increasing degree of apoptosis and inhibition of proliferation after exposure to various concentrations of Hsp70 inhibitors, including MAL3-101 and/or MAL3-101 derivatives, and the like or proteasome inhibitors, including MG-132, or both. Further, the method may comprise a result of a strong, synergistic apoptosis effect on one or more cell lines over a given amount of time. For example, there may be a strong effect observed after a given time course, after several hours, or a few days. Understanding the chaperoning effect may lead to the discovery of more effective proteasome inhibitors, Hsp70 inhibitors, and/or Hsp90 inhibitors.

With reference to the methods 100, 200, 300, 600, 700, 800, the combination therapy 400, and the composition of matter 500, the step of quantifying at least one result may refer to ascertaining the presence of at least one therapeutic effect of the administration, individually or in combination, of a candidate Hsp70 inhibitor, an Hsp70 inhibitor, a proteasome inhibitor, and an Hsp90 inhibitor. Therapeutic results include, for example, a complete response, a partial response, a minimal response, a stable disease condition, effective limiting of one or more adverse affects of the cancer, alleviation of one or more negative side affects associated with the cancer, or halting the spread/progression of the disease, or other therapeutic results, as may be desired. Quantification may refer to determining the relative toxicity level of the inhibitor, the dosage limits, the solubility, or the bioactivity thereof. The results may also be indicative of or factors in determining optimal delivery methods, treatment cycles, or dosage limits.

Figure 23A:
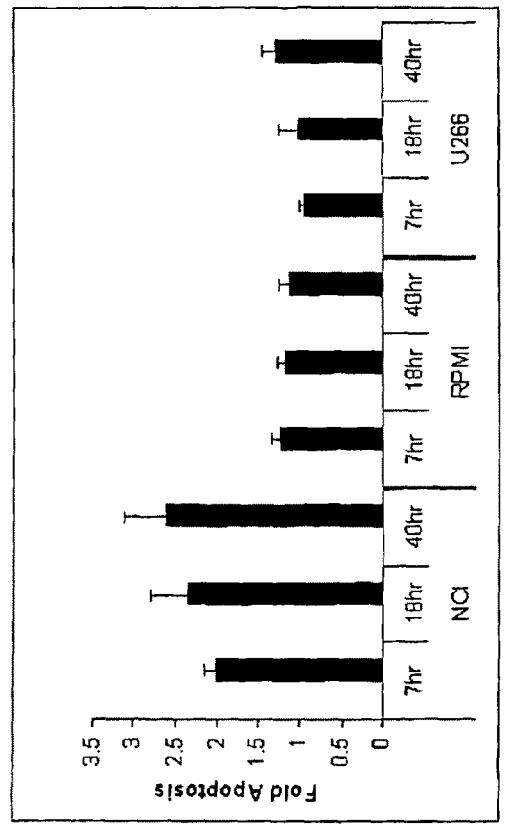
FIG. 23A is a chart of experimental data of three multiple myeloma cell lines to which MAL3-101 was administered, depicting fold apoptosis versus time course.
Figure 23B:
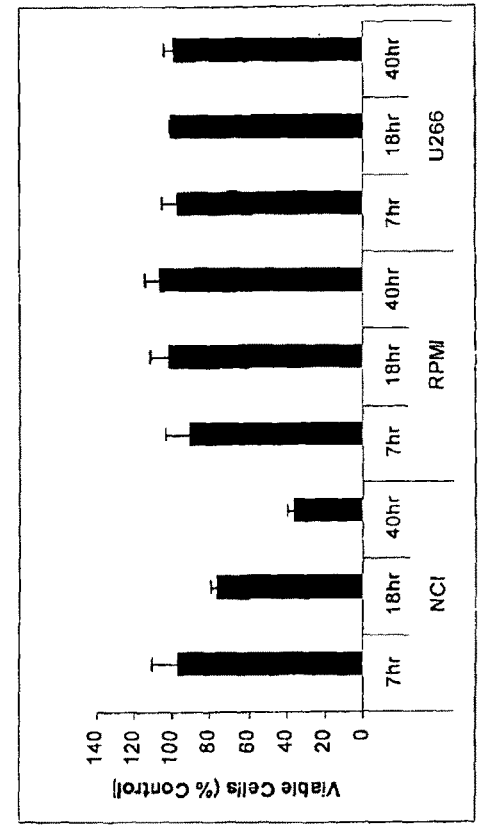
FIG. 23B is a chart of experimental data of three multiple myeloma cell lines to which MAL3-101 was administered, depicting percent of viable cells versus time course.

With reference to the various embodiments of the present invention, the dihydropyrimidinone MAL3-101 is shown to be an effective treatment for Hsp70 dependent cancers, including multiple myeloma when used individually. As is shown in FIG. 23A, and FIG. 23B, and specifically, FIG. 24 administering a concentration of 10 µM MAL3-101 showed beneficial results.

Further, the application or administration of both the dihydropyrimidinone MAL3-101 Hsp70 inhibitor and the proteasome inhibitor MG-132 exhibited synergistic, apoptotic results. With reference to FIGS. 26A, 26B, 27, 30, 31, and 36A through 36D, this is clearly shown. When MAL3-101 and MG-132 are administered in combination, the two inhibitors exhibit a synergistic result. A therapeutically effective amount of MAL3-101 may be of the range of 5 µM up to about 50 µM, with an $IC_{50}$ at 10 µM. It is also possible to employ a combination treatment of two or more of Hsp70 inhibitor MAL3-101, Hsp90 inhibitor 17-AAG, and/or proteasome inhibitor MG132, as is referenced in FIGS. 28, 29, 31, 32, 37A, 37B, and 40. Further a synergistic effect results from a combined Hsp70 inhibitor MAL3-101, Hsp90 inhibitor 17-AAG, and MG-132 proteasome inhibitor treatment. Synergy refers to a treatment in which the combined effects of two or more inhibitors taken together are greater than the additive affects of each, taken individually.

That is, as previously stated, MAL3-101 may exhibit a therapeutic effect at concentrations with a starting range of may be of 5 µM up to about 50 µM, with an $IC_{50}$ at 10 µM. MG-132 has a therapeutic effect on multiple myeloma cells at a concentration of the range of 0.05 µM up to about 10 µM. Contrastingly, the co-administration of sub-effective concentrations of both results in a synergistic effect. That is, the combined treatment of administering MAL3-101 and MG-132 in the range of 0.01 µM up to about 0.1 µM. Taken in a combined treatment, MG-132, which has long term toxicity affects associated with its current dosage and usage as a current treatment, may be administered a therapeutically effective treatment concentration at one-thousandth of its current treatment dosage. This synergistic result is plainly stated: apoptosis of the multiple myeloma cells. The correlation data may be further depicted by tables and figures disclosed and discussed in the experimental analysis and results section.

It should be noted that a subject in need thereof may include any living organism which may house one or more multiple myeloma cells. The organism may be one or more natural living or genetically engineered species for such, including, for example, mice, rats, dogs, cats, monkeys, humans, or any other mammal, reptile, or species of suitable nature and characteristics.

The reiterating step of one or more of the methods of the present invention may be used to repeat treatment cycles to a certain predetermined frequency. Reiterating co-administration or administration may be done in order to treat refractory or relapse multiple myeloma or Hsp-dependent cancer cells. The reiterating step 150 at least once may yield a treatment cycle, or planned method to treat a least one Hsp-dependent cancer cell. Further, it should be noted that the reiterating step 150 may be reiterated in order to effectively treat, provide a therapeutic result, or prevent future occurrences of refractory or relapse cancer from occurring.

Further, the method of cancer treatment may include the step of completing at least one additional cancer treatment or therapy. This step means to take into account that combinatorial drugs treatments and combination therapies that may often be more common practice in treating cancer. One reason for this may be that smaller doses of various types of drugs do not allow the cancer cells to build resistance to the drug, or evolve into a refractory type of cancer cell that is unaffected by the drug. Any of the cancer treatments previously articulated may be completed as a step in the current embodiment of the present invention. The additional cancer treatment may be selected from the group consisting of: chemotherapy, stem cell transplantation, radiation therapy, immunomodulatory agent therapy, thalomid therapy, aredia/zometa therapy, supportive care therapy, hormonal therapy, emerging therapy, and combinations thereof.

The composition of matter or the combination therapy may likewise be provided, for example, in a kit. The kit may include the combination therapy or the composition of matter for treatment of an Hsp70 dependent cancer in a pharmaceutically effective delivery means, and may further include, packaging and/or instruction provisions, as may be desired. The packaging may be useful to keep the various components together while preventing the various medicaments (inhibitors and bioactive delivery means or pharmaceutically acceptable agent) from environmental contamination. The instruction provision may include relevant information about direction for administering the therapy or composition, information relevant to the medicaments provided therein, and/or information related to the provider of the kit.

With reference to the methods 100, 200, 300, 600, 700, 800, the combination therapy 400, and the composition of matter 500, sub-effective concentrations may refer to the concentration, that, when individually administered, does not impute a measurable benefit or desired therapeutic affect to a plurality of cells. Sub-effective concentrations of the inhibitors may be calculated by utilizing various methods, including: according to a user's body weight, body surface area, progression of cancer/diagnosis, and/or cell resistance to the proteasome inhibitor and the Hsp70 inhibitor.

Still yet another example of an embodiment of the present invention provides a multiple myeloma treatment. The multiple myeloma treatment may comprise: an Hsp70 inhibitor, a proteasome inhibitor, and an Hsp90 inhibitor. The Hsp70 inhibitor may be MAL3-101, in a range of 0.01 μM to 0.1 μM. The proteasome inhibitor MG-132 may be in a range of 0.01 μM to 0.1 μM. Optionally, an Hsp90 inhibitor 17-AAG may be administered in a concentration range of 0.025 μM to 10 μM.

EXAMPLES

Example

Synthesis of Various MAL3-101 Derivatives and Production Method for MAL3-101

MAL3-101 may be disclosed and discussed in detail, including the synthesis of MAL3-101 and/or other dihydropyrimidinone compounds that may share characteristics and/or attributes which facilitate the practice of one or more embodiments of the present invention. Referenced herein, the MAL class of compounds may be referred to as pyrimidinone or pyrimidinone-peptoid. The MAL3 series of compounds were prepared by Ugi and Biginelli reactions, as may be shown in FIG. 2.

The Bignelli Reaction was a one-pot cyclocondensation of several reagents. In the reaction vessel, compound a (e.g. benzyl acetoacetate), compound b (e.g. 4-biphenyl aldehyde), and compound c (e.g. 6-ureidohexanoic acid) were stirred at room temperature in solvent d (e.g. tetrahydrofuran (THF)) with catalyst f (e.g. hydrochloric acid catalyst) for four days. The reaction yielded the Biginelli-pyrimidinones which were precipitated from solution using diethyl ether and hexanes at 76% yield. The compound was then characterized using liquid chromatography-mass spectrometry, and purity exceeded 90%.

Subsequently, an Ugi Reaction was performed on the Biginelli-pyrimidinone (compound g). The multicomponent reaction was stirred with compound g (e.g. the Biginelli-pyrimidinone MAL3-101 precursor), compound h (e.g. n-butyl isocyanide), compound i, and compound j while the mixture refluxed in solvent k (e.g. methanol) for 24 hours.

The MAL3-101 Ugi-Biginelli products (compound m) was purified by column chromatography and analyzed by LC-MS. Samples were stored at 4° C. in solution with dimethyl sulfoxide (DMSO).

To remedy what may be considered disappointing conversions under standard thermal conditions, microwave conditions may be utilized using the CEM Discover™ Microwave reactor, which increase reaction conversions. For example, a stirred solution of the various Biginelli-precursers, labeled MAL-precurser a through MAL-precursor d, and amine in methanol was treated with aldehyde and n-butyl isocyanide at room temperature. The mixture was then be heated twice at 70° C. for 20-30 minutes in a microwave reactor.

Alternatively, the reaction may be done with various β-ketoesters, aromatic aldehydes, and urea compounds to yield derivative compounds. The subsequent synthesis and structures of MAL3-38, MAL3-39, MAL3-54, MAL3-55, MAL3-90 and MAL3-101 are shown in FIG. 6 through FIG. 12. Further, various R groups that may be used to create various MAL3-101 derivatives may be shown in FIG. 3 through FIG. 5.

Experimental Methods

General Method for the Synthesis of Compounds in Class 1-5

The synthesis of MAL3-101 was accomplished by employing successive Biginelli and Ugi reactions to create a pyrimidinone-peptoid hybrid. In brief, benzyl acetoacetate and 6-ureidohexanoic acid were combined with p-biphenylcarboxaldehyde and reacted in a solution of tetrahydrofuran (THF) and HCl. The product, MAL2-11B, was combined with n-butylisocyanide, 5-formyl-2-methoxycarbonylmethoxybenzoic acid methyl ester, and n-hexylamine in an Ugi condensation reaction to create MAL3-101. The MAL3-101 derivatives were synthesized in similar reactions, but one reactant was altered to create an indexed library. The purities of the compounds were determined using a variety of methods (evaporative light scattering, total ion count/MS, and UV spectroscopy).

Synthesis of Class 1: Pyrimidinones

Compounds in this class were synthesized to contain only the heterocyclic pyrimidinone product of the Biginelli reaction. Various aldehyde compounds were utilized in each reaction.

Synthesis of methyl 6-ureidohexanoate (Class 2)

A solution of 6-ureidohexanoic acid (0.996 g, 5.72 mmol, 1.0 equiv) in methanol/benzene (2:7, 60 mL) was cooled to 0 degrees C., and a solution of trimethylsilyldiazomethane in hexanes (2.0 M, 3.43 mL, 6.86 mmol, 1.2 equiv) was added. The reaction mixture was warmed to room temperature and stirred for 1 h prior to removing all volatile components in vacuo. The crude methyl ester (1.06 g, 5.61 mmol, 98%) was used without further purification in the Biginelli reaction.

Synthesis of Pyrimidinone-peptoid Hybrids (Class 3-5)

Class 3 compounds utilize the compounds synthesized in Class 1 as the pyrimidinone building block, which is further reacted in the Ugi multicomponent condensation. Compounds in Class 4 and 5 utilize p-biphenylcarboxaldehyde as the aldehyde reagent in the Biginelli reaction and an assortment of aldehydes (Class 4) or esters (Class 5) in the Ugi reaction.

Synthesis of the MAL3-101 Diacid (Class 6) and DMT003024 (Class 7)

The MAL3-101 diacid was synthesized by reacting MAL3-101 with NaOH. DMT003024 (benzyl 1-(6-((1-(biphenyl-4-yl)-2-(butylamino)-2-oxoethyl)(2-morpholinoethyl)amino)-6-oxohexyl)-6-methyl-4-(4-nitrophenyl)-2-oxo-1,2,3,4-tetrahydropyrimidine-5-carboxylate) was prepared as follows: 4-phenylbenzylaldehyde (1.0 equiv) and 4-(2-aminoethyl) morpholine (1.0 equiv) were added at room temperature to a suspension of dihydropyrimidinone (1.0 equiv) in methanol. After stirring the reaction mixture for 10 min, n-butylisocyanide (1.0 equiv) was added and the reaction mixture was heated to reflux for 24 h. After cooling to room temperature and concentration in vacuo, the residue was extracted with EtOAc, washed twice with an aqueous 10% NaOH solution, once with brine, and dried (MgSO$_4$) prior to purification by chromatography on SiO$_2$ on an ISCO Companion chromatography system. The product was obtained as a 2:1 mixture of diastereomers based on $^1$H NMR integration of triplets at d 0.88 and 0.94 ppm, respectively. Major diastereomer: $^1$H NMR (300 MHz, CDCl$_3$) delta 8.06 (d, 2H, J=8.7 Hz), 7.62-7.25 (m, 14 H), 7.17-7.14 (m, 2H), 6.56 (br s, 0.8H), 5.90 (d, 0.4H, J=2.3 Hz), 5.44 (br s, 0.9H), 5.13 (d, 1H, J=12.2 Hz), 5.01 (d, 1H, J=12.2 Hz), 3.83-3.16 (m, 10H), 2.54 (s, 3H), 2.44-1.99 (m, 9H), 1.69-1.25 (m, 10H), 0.88 (t, 2H, J=7.2 Hz); $^{13}$C NMR (75 MHz, CDCl$_3$) d 173.6, 169.6, 165.3, 153.0, 150.3, 147.3, 141.3, 140.1, 135.5, 134.3, 133.2, 129.8, 129.4, 128.8, 128.4, 128.2, 127.6, 127.3, 127.2, 126.9, 123.8, 102.7, 66.5, 66.2, 53.5, 53.3, 39.3, 33.1, 31.3, 29.6, 26.4, 24.8, 19.9, 16.2, 13.6; MS (ESI) m/z (rel intensity) 859 ([M+H]$^+$, 100); HRMS (ESI) m/z calcd for C$_{49}$H$_{59}$N$_6$O$_8$ 859.4316, found 859.4377. Characteristic signals of minor diastereomer: $^1$H NMR (300 MHz, CDCl$_3$) delta 8.80 (br s, 0.2H), 6.27 (m, 0.4H), 5.53 (br s, 0.3H), 0.94 (t, 1H, J=7.2 Hz); 13C NMR (75 MHz, CDCl$_3$) delta 174.3, 170.1, 65.3, 62.4, 57.6, 56.8, 43.7, 39.5, 33.8, 32.1, 26.1, 20.2, 13.7.

Synthesis of N-(3-((tert-butylcarbamoyl-(4-iodophenyl)methyl)-(2-morpholin-4-ylethyl)carbamoylpropylbenzamide (MAL3-51)

According to the Fewell publication, which was incorporated by reference herein in its entirety, and referenced in the experimental examples above, 4-iodobenzaldehyde (0.982 g, 4.23 mmol), 4-(2-aminoethyl)morpholine (0.547 g, 0.552 mL, 0.423 mmol), 4-benzoylaminobutyric acid (0.877 g, 0.423 mmol), and tert-butylisocyanide (0.349 g, 0.474 microL, 0.423 mmol) in MeOH (10 mL) afforded MAL3-51 (2.02 g, 3.19 mmol, 75%) as colorless crystals after crystallization from ethyl acetate/hexanes (1:1): mp 109 degrees C; IR (film) 3261, 2966, 1712, 1677, 1552, 1119 cm$^{-1}$; $^1$H NMR (300.1 MHz, CDCl$_3$) delta 82 (d, 2H, J=8.3 Hz), 7.65 (d, 2H, J=8.3 Hz), 7.51-7.39 (m, 3H), 7.25 (t, 1H, J=4.8 Hz), 7.04 (d, 2H, J=6.1 Hz), 5.79 (s, 1H), 5.68 (s, 1H), 3.65-3.31 (m, 8H), 2.64-1.81 (m, 10H), 1.31 (s, 9H); $^{13}$C NMR (CDCl$_3$) delta 180.2, 174.2, 173.1, 141.8, 138.9, 137.9, 134.7, 131.7, 130.1, 95.4, 66.0, 61.8, 56.3, 52.1, 50.1, 42.0, 37.3, 28.0, 25.5, 20.9; MS (EI) m/z (rel intensity) 634 (M$^+$, 10), 522 (10), 113(40), 100 (100); HRMS (EI) m/z calculated for C$_{29}$H$_{39}$IN$_4$O$_4$ 634.2016, found 634.2022.

Example

Growing Cell Cultures, Cell Culture Information

Cultured cells were grown in a humidified incubator (37° C., 5% CO$_2$). Further, the Hsp-dependent cancer cell lines were MM cell lines, which are commercially available. MM cell lines may include, for example, U266, RPMI-8226, and NCI-H929, which may be obtained from American Type Culture Collection (ATCC, Manassas, Va.). The lines were grown in RPMI-1640 basal medium supplemented with 10% heat inactivated fetal calf serum (ATCC, Manassas, Va.) and antibiotics (100 Units/ml penicillin G, 100 µg/ml streptomycin).

Primary bone-marrow tumor cells and endothelial progenitor cells (EPCs) were obtained from previously untreated MM patients. That is, 10 ml bone marrow aspirates were collected in BD Vacutainers containing heparin (BD, Franklin, N.J.), and red cells may be removed from MM bone marrow samples using a Red Blood Cell Lysis Buffer (Roche Applied Science, Indianapolis, Ind.) to obtain primary tumor cells in marrow samples consisting of greater than 80% CD138-positive tumor cells, determined by flow cytometry as may be desired. Tumor cells were used for experiments the day they were harvested, and were cultured in the MM cell line medium described above.

For endothelial progenitor cells (EPC) outgrowth, bone marrow were further separated using Ficoll-Hypaque (Sigma Chemicals, St Louis, Mo.) density-gradient centrifugation and mononuclear cells were cultured (7×10$^6$ cells/well) in laminin-coated, 6-well plates (Becton Dickinson Labware, Bedford, Mass.) in EndoCult Basal Medium supplemented with 20% fetal bovine serum (StemCell Technologies, Vancouver, Canada) and antibiotics (100 U/ml penicillin G, 100 µg/ml streptomycin) until confluent. Under these culture conditions, EPC colonies were observed at 7 to 14 days, and confluence was reached 14 to 28 days. Outgrown EPCs were identified by the expression of endothelial and progenitor cell surface markers, including von Willebrand factor (a blood glycoprotein involved in coagulation), vascular endothelial-cadherin (where cadherins are a class of transmembrane proteins), vascular endothelial growth factor receptor-2, CD34, and CD133, as well as the absence of the MM marker CD38, determined by immunocytochemistry and flow cytometry. EPCs were passaged when they were 60-70% confluent by trypsin-ethylenediaminetetraacetic acid (EDTA) treatment (Invitrogen, Carlsbad, Calif.) onto 96-well culture plates (BD Biosciences, San Jose, Calif.).

Example

Cytotoxicity Assays

In the cytotoxicity assays, cells were at least 90% viable, and this was assessed by lack of uptake of trypan blue (Invitrogen, Carlsbad, Calif.). For cell survival assays, cells were plated in 96-well culture plates (BD Biosciences, San Jose, Calif.), 100,000 cells/well with 200 µl, of culture media. The effect of the drugs on cell survival was assessed, for example, by measuring 3-(4,5-dimethylthiazol-2-yl)-5-(3-car-boxymethoxyphenyl)-2-(4-sulphophenyl)-2H-tetrazolium, inner salt (MTS) (Promega, Madison, Wis.) dye absorbance of viable cells by adding 40 µL of 5 mg/mL MTS to each well for the last 4 hours of drug exposure. Additional wells containing cells only (untreated control) or medium only (background medium control) were used as controls. Absorbance at 490 nm ($A_{490}$) was measured using a spectrophotometer (Dynatech Laboratories, Chantilly, Va.). Viability was estimated according to the following formula:

$$\% \text{ Viable Cells} = \frac{A_{490}(\text{treated cells}) - A_{490}(\text{medium only})}{A_{490}(\text{untreated cells}) - A_{490}(\text{medium only})} \times 100\%$$

Each experiment was repeated at least three times. Every experimental condition was repeated at least in triplicate wells for every experiment. For cell death assays, $10^6$ MM cells were exposed to media or drug for the indicated incubation periods, washed with 1× phosphate-buffered saline (PBS), pH 7.4 (Invitrogen) and resuspended in 500 µL, binding buffer (Annexin V-PI detection kit (Immunotech/Beckman Coulter, Fullerton, Calif.), containing 1 µL, annexin V-fluorescein isothiocyanate (FITC) stock and 5 µL 20 µg/mL phosphatidylinositol (PI) to determinate the phosphatidylserine (PS) exposure on the outer plasma membrane. After incubation for 15 minutes at room temperature in the dark, the specimens were quantified by dual-color flow cytometry, acquiring 10,000 events. Cells that were Annexin V-FITC+ (with translocation of phosphatidylserine from the inner to the outer leaflet of the plasma membrane) and PI- (with intact cellular membrane) were considered as early apoptotic cells.

Example

Calculation of Combination Index (CI) and Inhibitory Concentration (IC)

Figures 26A, 26B:
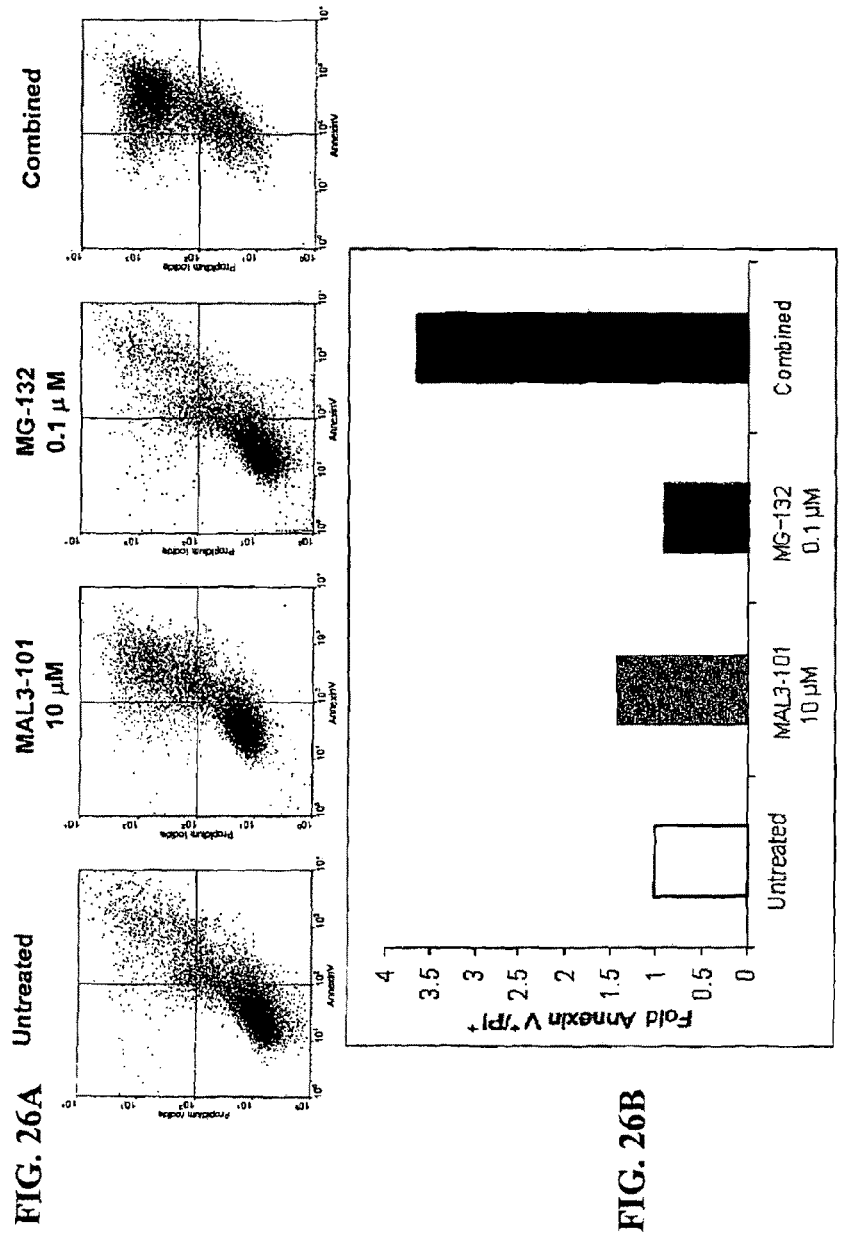
FIG. 26A is experimental data summarized as plots, depicting the apoptotic response of cells untreated; apoptotic response of cells treated with an Hsp70 inhibitor, MAL3-101; apoptotic response of cells treated with a proteasome inhibitor, MG-132; and apoptotic response of cells treated with combined Hsp70 inhibitor (MAL3-101) and proteasome inhibitor (MG-132).
FIG. 26B depicts experimental data summarized in a chart that details apoptotic response (by fold annexin release) versus treatment given to cells, including untreated, Hsp70 inhibitor treatment, proteasome inhibitor treatment, and combined treatment, which depicts an exemplary synergistic result.

To assess drug synergism (defined as a greater effect of drugs used in combination than the expected additive effects), a Combination Index, or CI, was calculated based upon the Chou-Talalay method. Briefly, the cellular fraction affected (Fa) was calculated based on an MTS assay after exposing cells to the drugs alone or in combination at a given dose compared to untreated cells, using the formula: Fa=100−% Viable Cells. Fa values were entered into Calcusyn software (Biosoft, Ferguson, Mo. and Cambridge, United Kingdom) to obtain CI values. CI values <1.0 indicated a synergistic effect of the drugs used in combination. For Inhibitory Concentration, or IC, calculations, dose-effect curves for MAL3-101, MG-132, 17-AAG, and their combinations were used to interpolate the median inhibitory concentration that caused 30% ($IC_{30}$), 50% ($IC_{50}$), and 70% ($IC_{70}$) reductions in the % viable cells compared to untreated cells. These results are depicted in FIG. 25A and FIG. 26A.

Example

Reverse Transcription (RT)-PCR Analysis

Total RNA was prepared from NCI-H929 and HEK293 cells using TRIzol reagent (Invitrogen, Carlsbad, Calif.) following exposure to MAL3-101, MG-132, and 17-AAG alone and in combination at the indicated time points. Tunicamycin was used at varying concentrations.

Total RNAs were used for the first-strand synthesis with the Superscript reverse transcriptase (Invitrogen, Carlsbad, Calif.). PCR primers (5'-ACACGCTTGGGAATGGACAC-3' [Seq. ID No. 1] and 5'-CCATGGGAAGATGTTCTGGG-3' [Seq. ID No. 2]) encompassing the missing sequences in XPB-1s were used for the PCR amplification with AmpliTaq Gold polymerase (Applied Biosystem, Foster City, Calif.) with a probe set spanning the spliced-out region. PCR products were separated by electrophoresis on a 3% agarose gel (Agarose-1000, Invitrogen) and visualized them by ethidium bromide staining to assess the degree of X-box binding protein-1 unspliced (XBP-1u, ~280 bp) and spliced (XBP-1s, ~265 bp) mRNA.

Example

Statistical Analysis

Survival data are expressed relative to cells treated with medium alone in the absence of drugs. All experiments were performed in triplicate and duplicated at least twice. The bars on one or more of the FIGs. which are depicted as charts indicate standard deviation between replicate experiments. Statistical significance of differences between drug-treated versus medium-treated cultures were determined using Student's t test (At test is any statistical hypothesis test in which the test statistic has a Student's t distribution if the null hypothesis is true), and statistical significance was set at P≤0.05.

Example

Results

Multiple myeloma cell lines NCI-H929, RPMI-8266 and U266 were exposed to MAL3-101 at a concentration of 10 µM for the indicated culture periods. NCI-H929, RPMI-8226, and U266 samples (each at $1 \times 10^5$ MM cells) were exposed, in triplicate, to 10 µM MAL3-101, for indicated culture periods. [M represents Molarity, the number of moles of a given substance per liter of solution.] Cytotoxicity was induced, and as FIG. 23A and FIG. 23B show, NCI-H929 cells was the most sensitive to the cytotoxic effects of this compound as reflected by its stimulation of apoptosis FIG. 23A and inhibition of survival FIG. 23B compared to the other cell lines (RPMI and U266). The antimyeloma effects of MAL3-101 on survival and apoptosis of NCI-H929 cells increased progressively until 40 hr of exposure. While still longer exposure to the cell lines may be computed, longer exposure may not result in a significant change in survival or apoptosis. As is shown by FIG. 23A and FIG. 23B, MAL3-101 induces a graded cytotoxic effect in MM cell line NCI-H929 after 7, 18, and 40 hr exposure. FIG. 23A depicts the fold apoptosis compared to untreated cells. This was determined by immunofluorescence and flow cytometric analysis of annexin V-positive, PI-negative cells. FIG. 23B depicts the percent viability of MM cell lines compared to untreated cells. This was assessed by an MTS assay. Error bars on FIG. 22A and FIG. 23B represent the standard deviation between three experiments.

Figure 24:
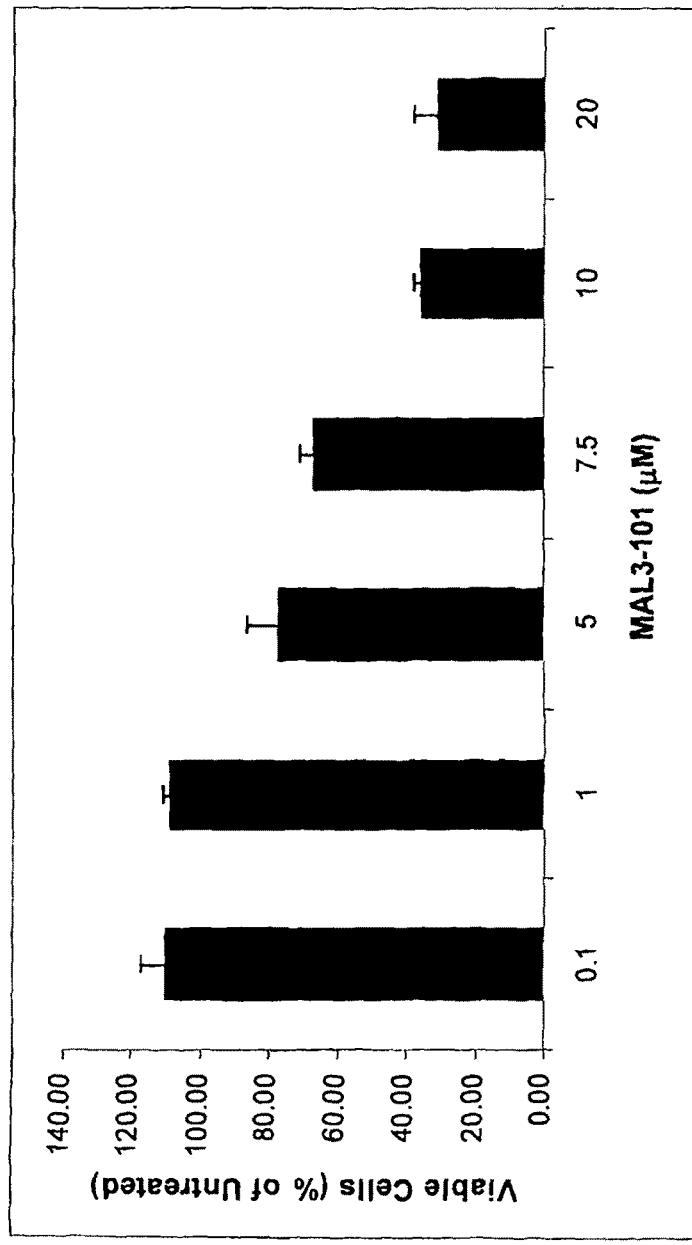
FIG. 24 is a chart of experimental data of dose response of three multiple myeloma cell lines to which MAL3-101 was administered, depicting percent of viable cells versus dosage (in micromolar).

Dose response studies were completed, and FIG. 24 depicts the MAL3-101 production of a dose-responsive cytotoxic effect in MM cell line NCI-H929. NCI-H929 samples (each sample at $1 \times 10^5$ MM cells) were exposed to the indicated concentrations of MAL3-101. As depicted in FIG. 24, at 40 h of exposure, the IC$_{50}$ of MAL3-101 is 8.3 µM. Percent viability compared to untreated cells was assessed by an MTS assay after 40 hr exposure. Error bars represent standard deviation from three separate experiments.

Referring to FIG. 25A through 25C, the apoptotic response of MAL3-51 and MAL3-101 MM cell line NCI-H929 are compared. FIG. 25A illustrates that MAL3-51, is a less potent Hsp70 antagonist than MAL3-101. This may indicate that the cytotoxic effects of MAL3-101 are directly related to its ability to inhibit Hsp70. NCI-H929 cells (sample size 1×10$^5$ MM cells) were exposed to 10 µM of MAL3-101 or MAL3-51 for 40 h. The fold apoptosis compared to untreated cells was determined by flow cytometric analysis of annexin V-positive, PI-negative cells. Error bars represent standard deviation from three independent experiments. FIGS. 25B and 25C also illustrates the molecular structures of the two compounds, MAL3-101 and MAL3-51, respectively, to contrast their respective structures.

Hsp70 gene expression is upregulated in MM cells, especially after proteasome inhibition, which disrupts degradation of ubiquinated immunoglobulins and causes apoptosis and inhibition of MM cells. Therefore, the antimyeloma effects of MAL3-101 may potentiate the antimyeloma effects of proteasome inhibition. This may be depicted, for example, in FIG. 26A and FIG. 26B. FIG. 26A and FIG. 26B illustrate that MAL3-101 in combination with MG-132 produces an enhanced effect on apoptosis of MM cell line NCI-H929. Specifically, FIG. 25 depicts that 1×10$^5$NCI-H929 cells were cultured in the presence or absence of 10 µM of MAL3-101; 0.1 µM of MG-132; or, of their combination. After 18 h of culture cells were stained by immunofluorescence for annexin V-FITC and propidium iodide-PE, and analyzed by flow cytometry to determine the percent of apoptotic cells, shown by two-color dot plots. Quadrants were set based upon isotype-specific controls for FITC and PE (not shown in FIG. 26A). Representative results from one of three experiments are shown, as depicted in FIG. 26A. Specifically, FIG. 26B depicts a bar graph summarizing the dot plots (as depicted in FIG. 26A) where the percent of total apoptotic cells quantitated by flow cytometry are shown relative to untreated cells.

As is shown in FIG. 26A and FIG. 26B, when NCI-H929 cells were simultaneously exposed to a combination of MAL3-101 (10 µM), and the proteasome inhibitor MG-132 (0.1 µM), significant apoptosis was induced as early as 18 hours after exposure. At this time point, neither drug alone was effective in inducing apoptosis, indicating the presence of synergism between the antimyeloma effects of MAL3-101 and MG-132 (FIG. 26A, FIG. 26B).

Figure 27:
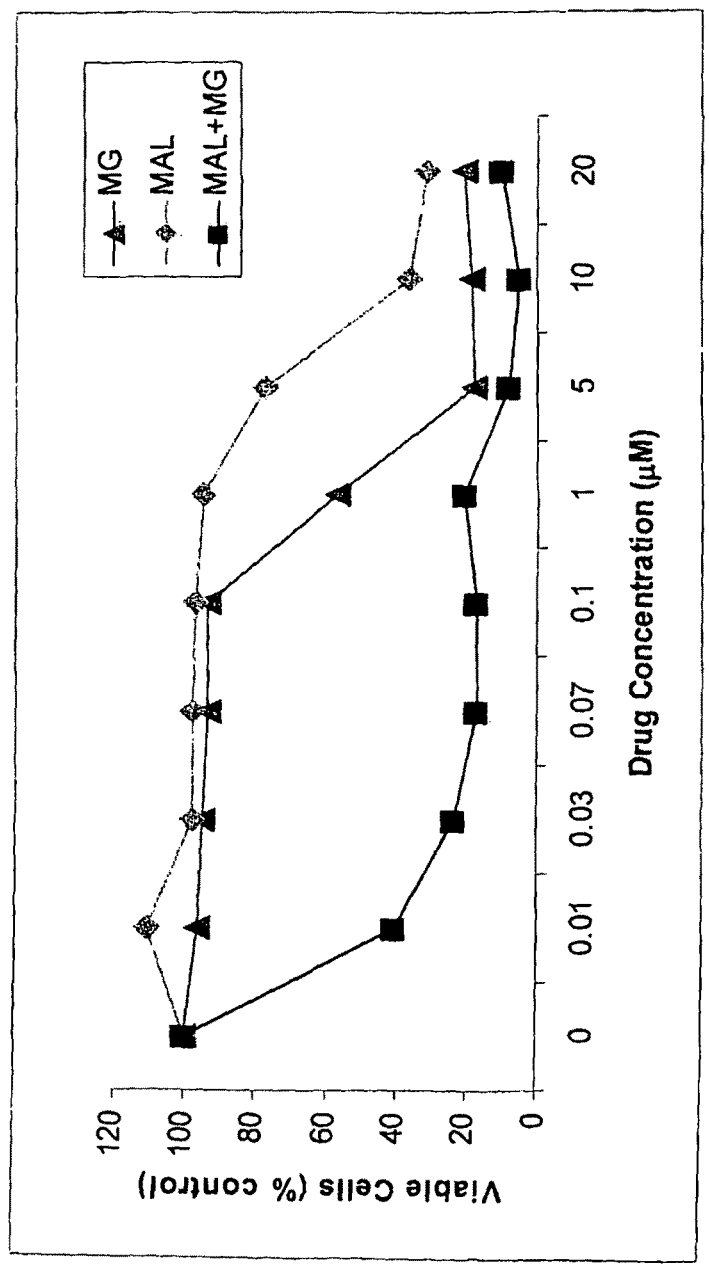
FIG. 27 is a plot of experimental data showing the percent of viable cells versus concentration in μM of treatment, where the three different lines depict different treatments, including a proteasome inhibitor treatment, an Hsp70 inhibitor treatment, and a combined treatment.

Next, the effects of MAL3-101 and MG-132 on survival of NCI-H929 cells were examined alone or in combination over a range of concentrations (0.01-20 µM), after 40 h of exposure in order to maximize their cytotoxic effects. That is, 1×10$^5$NCI-H929 cells were exposed, in triplicate, to MAL3-101, or MG-132 alone or in combination, at equal concentrations as indicated, for 40 hrs. Cell survival was assessed by an MTS assay is shown as percent of untreated cells. Representative data from one of three independent experiments are shown as the results plotted on the chart of FIG. 27. Referring to FIG. 27, the IC$_{50}$ of MG-132, in the absence of MAL3-101, was 1 µM. In the presence of MAL3-101, at ineffective concentrations of either drug, the IC$_{50}$ of MG-132 was increased dramatically to 0.01 µM. As shown in the trend of the various plots depicted in FIG. 27, MAL3-101 and MG-132 trigger synergistic cytotoxicity in MM cell line NCI-H929.

Synergistic cytotoxicity was strongly indicated by Combination Index (CI) values of less than 1, which was observed when MAL3-101 and MG-132 were combined in equal concentrations ranging from 0.01 µM-0.10 µM, all of which reduced the viability >50% (effect >0.5). The concentrations of MG-132, MAL3-101, Viability, Fa, and Combination index are all shown in the table of FIG. 30. FIG. 30 depicts the trend that MAL3-101 and MG-132 induce synergistic cytotoxicity in MM cell line NCI-H929. Synergistic cytotoxicity (indicated by CI values <1), is observed in equal combination doses ranging from 0.01-0.10 µM MAL3-101 and MG-132, all of which reduced the viability >50% (effect >0.5). In contrast, these combination concentration values are far less than the therapeutic effect ranges needed for each of the compounds individually, that is, 5 µM to 50 µM for MAL3-101, and 0.05 µM to 10 µM for MG-132.

Figure 28:
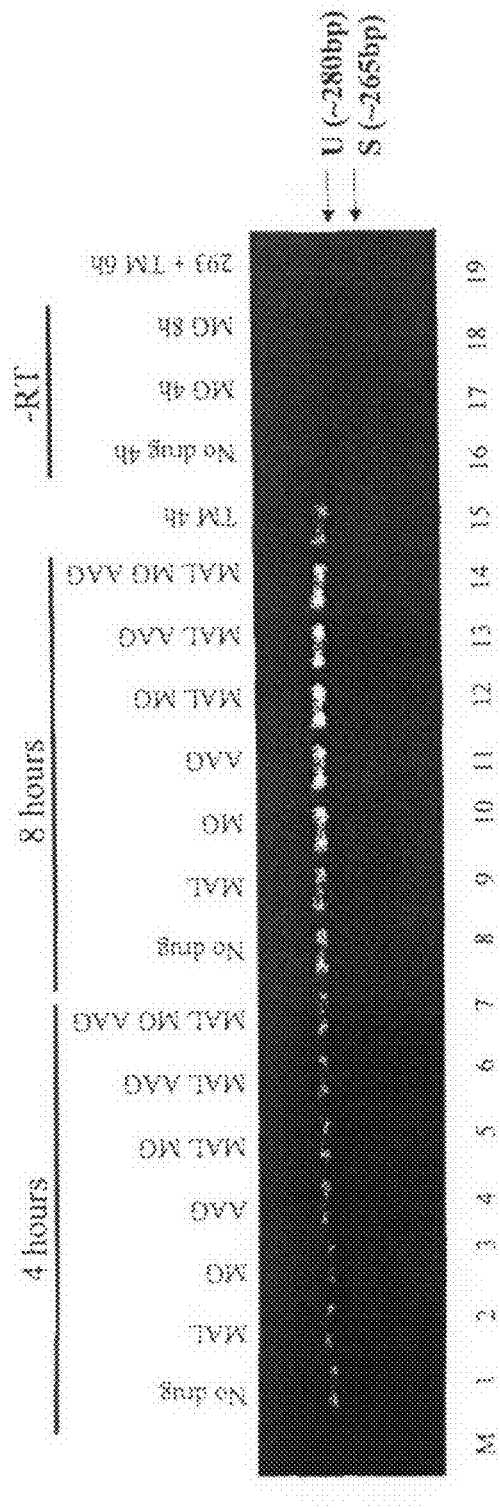
FIG. 28 is experimental data depicting induction of the unfolded protein response, indicated by the ~265 bp "S" message, after various treatments, including no treatment, proteasome inhibitor treatment, Hsp70 inhibitor treatment, Hsp90 inhibitor treatment, and combinations thereof over a time course.

To understand why MAL3-101 and MG-132 individually and in combination impact the viability of NCI-H929 cells, one must examine whether the unfolded protein response (UPR) was induced at early time points after administration of the compounds. FIG. 28 provides a depiction of the absence of XBP-1 splicing in NCI-H929 cells in response to chaperone and/or proteasome inhibition at early time points. To understand the impact of the viability of NCI-H929 cells, RT-PCR (reverse transcriptase-polymerase chain reaction) analysis of XBP-1s mRNA levels in NCI-H929 was performed after 4 and 8 hr untreated or exposed to 7.5 µM MAL3-101, 0.2 µM MG-132, and 0.5 µM 17-AAG alone and in combination. Tunicamycin (TM) was used as a control for UPR induction, and shows XBP-1 splicing in NCI-H929 and HEK293 cells exposed for 4 and 6 hr, respectively.

The signaling pathways upregulated in UPR include downstream events from ATF-6 translocation to nucleus, splicing of transcription factor XBP-1, and inhibition of global protein translation via inactivation of the elongation factor eIF2. Since XBP-1 regulates downstream effects of UPR, and recent experiments indicate a role for XBP-1 in immunoglobulin secretion, plasma cell differentiation, and more recently, progression of MM, MAL3-101 effects of XBP-1 splicing in MM cells were focused on. Early time points were chosen because UPR induction is attenuated at later times, most likely because of compensatory cellular responses. As shown in FIG. 28, there does not appear to be an effect of MAL3-101 on XBP-1 splicing in NCI-H929 cells before or after drug exposure. While XBP-1 splicing was in positive control, NCI-H929 cells were treated for 4 hours with tunicamycin, which induces ER stress by inhibiting N-linked glycan addition. Stronger XBP-1 splicing was observed in the non-tumor cell line HEK293 treated with tunicamycin for 6 hours. Consistent with these data, the levels of BiP, an ER lumenal chaperone whose synthesis is enhanced upon downstream of ATF6 activation, did not change under any of the examined conditions (data not shown) indicating that the first two phases of UPR were not active players in MAL3-101 effects on MM. The effects of MAL3-101 on global protein translation, and eIF2 activation, and caspases activated by MAL3-101 are currently being investigated.

Figure 29:
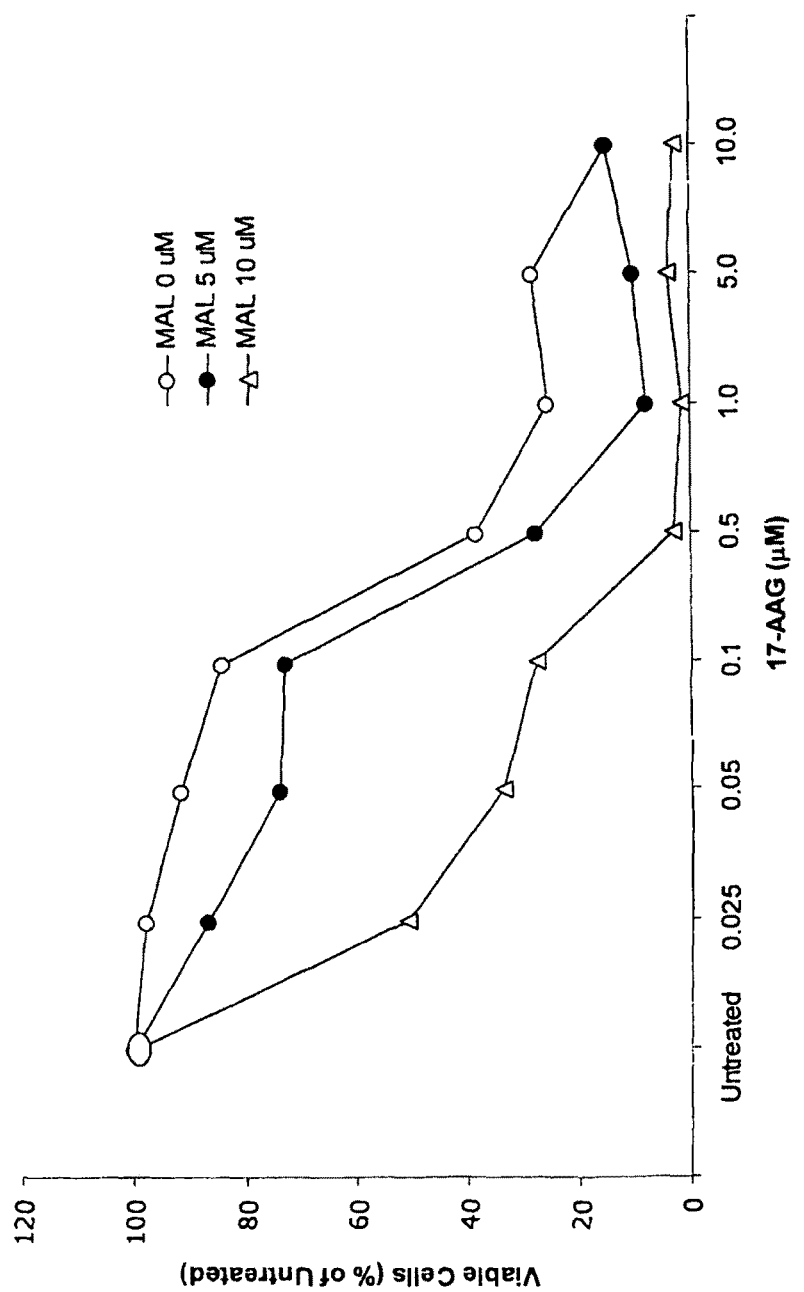
FIG. 29 is a plot of experimental data depicting the percent viable multiple myeloma cells after combined treatment with an Hsp70 inhibitor (MAL3-101) and an Hsp90 inhibitor (17-AAG) in differing concentrations.

To assess the potential antimyeloma and synergistic effects of Hsp70 and Hsp90 inhibition in MM, NCI-H929 cells were exposed for 40 h to a combination of MAL3-101 and the Hsp90 inhibitor 17-AAG at a range of concentrations (0.025-10 µM). Results from one of three representative experiments are shown in FIG. 29, where the IC$_{50}$ of 17-AAG was 0.4 µM, and in combination with either 5 or 10 µM of MAL3-101 was reduced to 0.3 and 0.03 µM, respectively. This indicates that MAL3-101 significantly enhanced the antimyeloma effect of 17-AAG at concentrations of 0.025-1 µM. FIG. 29 is a chart depicting that MAL3-101 and 17-AAG trigger synergistic cytotoxicity in the MM cell line NCI-H929. NCI-H929 cells were exposed to 17-AAG (0-10 µM) alone (white circles) or in combination with either 5 µM (black circles) or 10 µM (white triangles) of MAL3-101 for 24 hours. Viability as assessed by an MTS assay is shown as percent of untreated cells. Representative data from one of three experiments are shown.

As shown in the table of FIG. 31, the synergistic cytotoxicity was strongly indicated by Combination Index values of less than 1. This was observed in combination with 0.05-1.0 µM 17-AAG and the indicated concentrations of MAL3-101, all of which reduced the viability >50% (effect >0.5) with 10 µM MAL3-101. FIG. 31 indicates that MAL3-101 and 17-AAG induce synergistic cytotoxicity in the MM cell line NCI-H929.

Taken together, these results strongly suggest the potential clinical benefit of combining Hsp70/Hsp90 inhibitory therapies in MM, and that using a combination of MAL3-101 and 17-AAG with a proteasome inhibitor may provide an even more potent antimyeloma effect than is now clinically available as suggested by the reduction in $IC_{50}$ values of the combinations shown in the table depicted as FIG. 34. As referenced in the table of FIG. 32, the summarized experimental depicts that MAL3-101, MG-132, and 17-AAG inhibitory concentrations produce graded cytotoxic effects alone and in combination on MM cell line NCI-H929.

Discussion:

Results of the various examples indicate that MAL3-101, a small molecular inhibitor of Hsp70, exerts antimyeloma effects on both MM cells and cell lines, as well as on the tumor microenvironment in MM. Furthermore, results show that MAL3-101 sensitizes MM cells to proteasome inhibitor MG-132, so that potent cytotoxic effects are obtained with this drug at nano-molar concentrations which when used alone are not effective. Lastly, combination of subeffective cytotoxic concentrations of both drugs result in significant antimyeloma cytotoxicity in MM cell lines. The mechanism(s) responsible for the cytotoxic actions of MAL3-101 alone or in combination with proteasome inhibition are currently the subject of additional research by the inventors of the present invention.

An important conclusion that can be drawn from these results is that Hsp70 gene and protein upregulation may be a specific and important anti-apoptotic mechanism that promotes growth and survival of MM tumor and its microvascular environment. The significance of Hsp70 in MM underscores the importance of the endoplasmic reticulum (ER) stress pathway as a treatment target in MM as suggested by earlier studies, and extends and confirms this thesis by demonstration of the potent anti myeloma effects of MAL3-101 alone or in combination with other inhibitors of this pathway.

One of the essential characteristics of MM cells is their increased synthesis and secretion of monoclonal immunoglobulin. These immunoglobulins are folded into their tertiary structures within the (ER) of the multiple myeloma tumor cells (MM cells).

Within the ER as a response to the increased protein production, unfolded protein response (UPR), results in an upregulation in protein folding via activation of chaperone proteins involved in protein folding and trafficking, as well as to an increase in degradation of misfolded proteins via the ubiquitin-proteasome pathway in order to confer a survival signal and protect the cells from downstream apoptotic effects of an escalating, unopposed ER stress signal. Inhibition of both UPR associated response pathways are shown to be effective antimyeloma strategies.

First, downstream effects of proteasome inhibition by PS-341 (Bortezomib, MG-132), a 26S proteasome inhibitor, has resulted in one of the most effective antimyeloma strategies available for treatment of newly-diagnosed and relapsing MM, indicating that interference with ER stress response is a rational antimyeloma strategy.

Second, results of highthrough output analyses show that effective proapoptotic pathways are activated and antiapoptotic pathways are inhibited as a consequence of interference of degradation of ubiquinated proteins by PS-341 in MM cells. To salvage proteins from degradation, chaperones including Hsp70 and Hsp90 are upregulated and new proteasome synthesis is triggered in MM cells, leading to the prediction that inhibition of chaperones and development of novel proteasome inhibitors would potentiate the effectiveness of existing antimyeloma strategies. Since Hsp70 levels increase upon UPR induction, and in addition to its role in tempering the UPR, this chaperone is generally considered to be the most potent antiapoptic chaperone in the cell Hsp70 inhibition was a strong candidate for an effective means to kill MM cells and/or exhibit synergistic effects with proteasome inhibitors.

As a result, exposure to Hsp70 inhibitor MAL3-101 sensitized the MM cells to subtoxic concentrations of the proteasome inhibitor MG-132. Furthermore, MAL3-101 also sensitized MM cell line NCI to cytotoxic effects of Hsp90 inhibitor 17-AAG. This indicates that coupling of interference with ER stress pathway at protein folding and transport level is potentially a very effective antimyeloma strategy as well.

Although Hsp70 and Hsp90 are up-regulated globally in almost all cancers, Hsp70 and Hsp90 are required for the survival of different cancer cells. Hsp70 is required for breast cancer cells to survive but Hsp90 is required for small cell lung carcinomas to survive (and grow), thus the role of the chaperones and their inhibitors in MM, and B cell ontogeny will be critical.

Similarly, in several cells targets of Hsp70 and Hsp90 were shown to be different protein substrates, and when the two chaperones do interact with the same substrate, the Hsp70 and Hsp90 often have distinct effects on the fates of the substrate. For example, for apoB, both Hsp70 and Hsp90 help degrade the protein, but for CFTR (the protein that when mutated causes cystic fibrosis) Hsp90 is pro-folding but Hsp70 is pro-degradative, so, one protects the protein and the other helps destroy it.

Thus, determining the targets of the chaperones in other MM cell lines, and primary MM cells and in vivo tumors is a key goal for evaluation and application of the results to clinic because the targets may indicate MM cell sensitivity to these agents and thus help determine patients who will best benefit from inhibitors of chaperones and/or inhibitors of ER stress pathway in general. Taken together, the experimental results herein show that exposure to MAL3-101 significantly potentiates the effects of other protein quality control inhibitors in MM cells.

Further, primary bone marrow MM cells from five untreated patients as well as their bone marrow endothelial progenitor cells (EPCs) exhibited sensitivity to dual targeting with MAL3-101 and MG-132. Based on these results, it appears as though Hsp70 is an important new target to treat MM, and that MAL3-101 is one of a class of first-generation lead compound to hasten the demise of MM cells, to overcome resistance to proteasome inhibitors by allowing dose reduction, while potentiating the effects of other inhibitors of UPR. Furthermore, experimental evidence suggests that heat shock proteins may be upregulated in response to apoptotic effects of other myeloma-modulating enzymes as well, for example histone deacetylases and microtubule inhibitors with antimyeloma effects are shown to be associated or upregulated respectively by Hsp70 indicating that MAL3-101 may be means to inhibit resistance development to a wide range of antimyeloma drugs.

Materials and Methods: Reagents and Cell Cultures:

MAL3-101 (the structure is shown as the final product in FIG. 12, in FIG. 13, and in FIG. 25B), the proteasome inhibitor MG-132 (A.G. Scientific, San Diego, Calif.) and the Hsp90 inhibitor 17-allylamino-17-demethoxygeldanamycin (17-AAG) (Calbiochem/EMD Biosciences, San Diego, Calif.) were dissolved in dimethylsulfoxide (DMSO; Sigma-Aldrich, St. Louis, Mo.), and stored at $-20°$ C. Final concentration of DMSO was 0.03% and this was used to treat control cells. The MM cell lines examined were NCI-H929, RPMI-8226, and U266 (ATCC, Manassas, Va.). Normal peripheral blood mononuclear cells (PBMC) and bone marrow (BM) cells were obtained from StemCell Technologies (Vancouver, Canada). Primary MM cells and EPCs were from BM aspirates of newly-diagnosed patients following informed consent. MM cells were enriched to >95% $CD138^+$ cells by positive selection, using anti-CD138 MACS Microbeads according to the manufacturer's instructions (Miltenyi, San Diego, Calif.). EPCs were derived from BM aspirates of newly diagnosed patients, maintained in EndoCult medium (StemCell Technologies), and used at first passage as previously described in: H. Zhang, V. Vakil, M. Braunstein, E. L. Smith, J. Maroney, L. Chen, K. Dai, J. R. Berenson, M. M. Hussain, U. Klueppelberg, A. J. Norin, H. O. Akman, T. Ozcelik, O. A. Batuman, Circulating endothelial progenitor cells in multiple myeloma: implications and significance, Blood 105 (2005) 3286-3294; and M. Braunstein, T. Ozcelik, S. Bagislar, V. Vakil, E. L. Smith, K. Dai, C. B. Akyerli, O. A. Batuman, Endothelial progenitor cells display clonal restriction in multiple myeloma, BMC Cancer 6 (2006) 161, which are incorporated herein by reference. Cell lines, PBMC and BM cells were maintained in RPMI-1640 supplemented with 10% heat-inactivated fetal calf serum in the referenced Zhang and Braunstein references.

Cytotoxicity Assays:

Cells ($1 \times 10^5$) were plated in 96-well microtiter plates (Costar, Cambridge, Mass.) in 100 μL, of growth medium and exposed for indicated periods to various concentrations of compounds or their combinations. Control cells were cultured in DMSO. All studies were performed in triplicate and repeated at least three times independently. Survival was measured by an MTS assay (Promega, Madison, Wis.) as per the manufacturer's directions. The absorbance ($A_{450}$) ratio of treated to untreated cells, after the subtraction of background absorbance, was multiplied by 100 to obtain percent cell survival. Cell death was measured by trypan blue dye exclusion in identically plated cultures.

Apoptosis induction in control (DMSO-treated) or inhibitor treated cells was determined using an Annexin-V-FLUOS Staining Kit according to the manufacturer's instructions (Roche, Indianapolis, Ind.). Briefly, cells ($1 \times 10^5$) were harvested at indicated time points after treatment, and Annexin V-fluorescein isothiocyanate (FITC) and propidium iodide (PI) were added to individual samples and incubated for 30 min in a dark environment. Fluorescence was analyzed by a FACSort flow cytometer (BD Biosciences, San Jose, Calif.) by acquiring 10,000 events per sample.

Cell Cycle Analysis:

Cell cycle analysis of control (DMSO-treated) or MAL3-101-treated NCI-H929 ($2 \times 10^5$) was assessed by PI staining and FACS analysis of samples. Resulting DNA distributions were analyzed for the proportions of cells in $G_0/G_1$ and $G_2/M$ phases of the cell cycle after subtractive gating of cell doublets and debris as described in G. Anderson, M. Gries, N. Kurihara, T. Honjo, J. Anderson, V. Donnenberg, A. Donnenberg, I. Ghobrial, M. Y. Mapara, D. Stirling, D. Roodman, S. Lentzsch, Thalidomide derivative CC-4047 inhibits osteoclast formation by down-regulation of PU. 1, Blood 107 (2006) 3098-3105, which is incorporated herein by reference.

Western Blotting:

Whole-cell lysates were prepared using the Mammalian Cell Lysis Kit (Sigma-Aldrich) and analyzed by Western blot analysis as described in the Zhang reference, cited supra, which is incorporated herein by reference. Equal amounts of protein were separated by SDS-PAGE and electrotransferred onto a nylon membrane. Primary antibodies to detect caspase-3 (Cell Signaling Technology, Danvers, Mass.), poly (ADP-ribose) polymerase (PARP; Abcam, Cambridge, Mass.), and β-actin (Sigma Aldrich) were used along with a HP-conjugated goat-anti-mouse polyclonal secondary antibody (BD Biosciences, Franklin Lakes, N.J.). Enhanced chemiluminescence (ECL) substrate (Pierce Biotechnology, Rockford, Ill.) was used for antibody detection.

Reverse-transcription Polymerase Chain Reaction (RT-PCR) Analysis of XBP1 mRNA Splicing:

Unspliced (XBP-1u, 285 bp) and spliced (XBP-1s, 259 bp) XBP-1 mRNA levels of treated NCI-H929 were determined by PCR amplification of total RNA that was reverse transcribed by SuperScript Reverse Transcriptase (Invitrogen, Carlsbad, Calif.). PCR primers (5'-TTACGAGAGAAAACT-CATGGC-3' [Seq. ID No. 1] and 5'-GGGTCCAACTTGTC-CAGAATGC-3' [Seq. ID No. 2]), which flank the 26-nt intron of XBP1 mRNA, were used for PCR amplification with Ex Taq polymerase (Takara Bio, Shiga, Japan).

Human Immunoglobulin Light-chain Enzyme-linked Immunosorbent Assay (ELISA):

Levels of secreted and intracellular κ (kappa) and λ (lambda) light chains (LCs) were determined using Human Kappa and Lambda (bound and free) ELISA Quantitation Kits (Bethyl Laboratories, Montgomery, Tex.) according to manufacturer's instructions. Pellets and supernatants were obtained from $10^6$ cells cultured in serum-free medium overnight. Total protein in whole-cell lysates from cell pellets and supernatants was determined using the Bio-Rad Protein Assay (Bio-Rad Laboratories, Hercules, Calif.), and 500 ng total protein was used in each ELISA. To account for differences in secretion relative to synthesis of LCs between MM cell lines, LC production was assessed as the fraction of secreted over intracellular LC.

Statistical Analysis:

DMSO-treated cultures were compared to drug-treated cultures by Student's t tests or by Dunnett's post-hoc test following significant repeated-measures one-way analysis of variance. All tests were two-tailed, and statistical significance was set at $P \leq 0.05$. Isobologram analysis was performed to derive combination index (CI) values based upon the Chou-Talalay method using CalcuSyn software (Biosoft, Ferguson, Mo. and Cambridge, United Kingdom) as described in L. Catley, E. Weisberg, T. Kiziltepe, Y. T. Tai, T. Hideshima, P. Neri, P. Tassone, P. Atadja, D. Chauhan, N. C. Munshi, K. C. Anderson, Aggresome induction by proteasome inhibitor Bortezomib and {alpha}-tubulin hyperacetylation by tubulin deacetylase (TDAC) inhibitor LBH589 are synergistic in myeloma cells, Blood (2006), which is incorporated herein by reference.

Results: MAL3-101 Suppresses Growth and Initiates Apoptosis in Human MM Cells:

To determine the effect of MAL3-101 on MM cell lines, cells were cultured with increasing concentrations of MAL3-101 and harvested at different time points. Control cells were treated with vehicle (DMSO). The highest level of cytotoxicity was observed in NCI-H929 (FIG. 34A); dose-response studies at 40 h exposure showed the $IC_{50}$ to be 8.3 µM (FIG. 34B). Exposure to MAL3-101 beyond 48 h did not result in additional increases in cell death or apoptosis (data not shown). In contrast, there was no response to 10 or 20 µM MAL3-51 (FIG. 34B), a substantially less potent Hsp70 modulator, strongly suggesting that the cytotoxic effect of MAL3-101 was directly related to its ability to inhibit Hsp70 in NCI-H929.

Figure 34A:
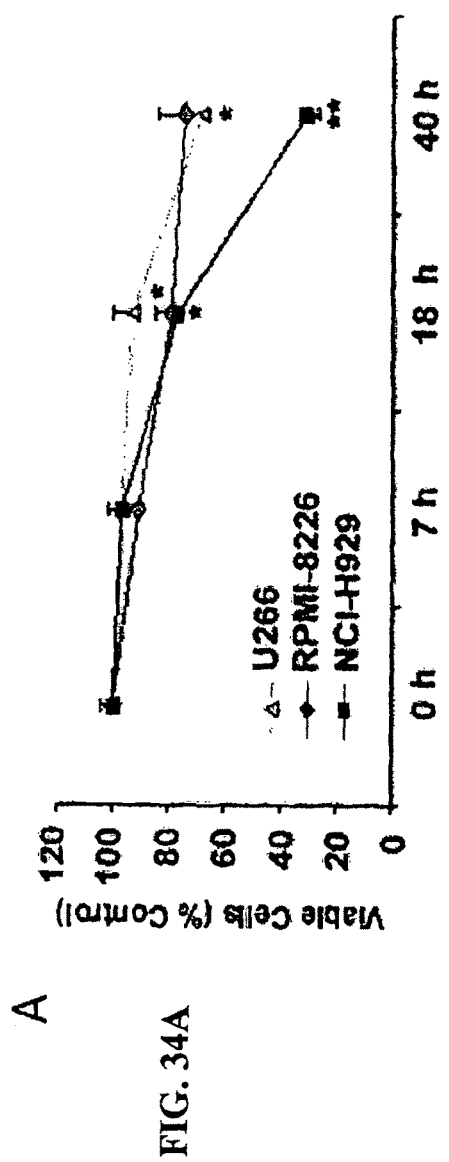
FIG. 34A illustrates a chart of three MM cell lines ($1 \times 10^5$) which were exposed to 10 μM MAL3-101 for the indicated culturing periods, showing the fold change in percent viable cells in treated versus control cells as determined by an MTS assay.
Figure 34B:
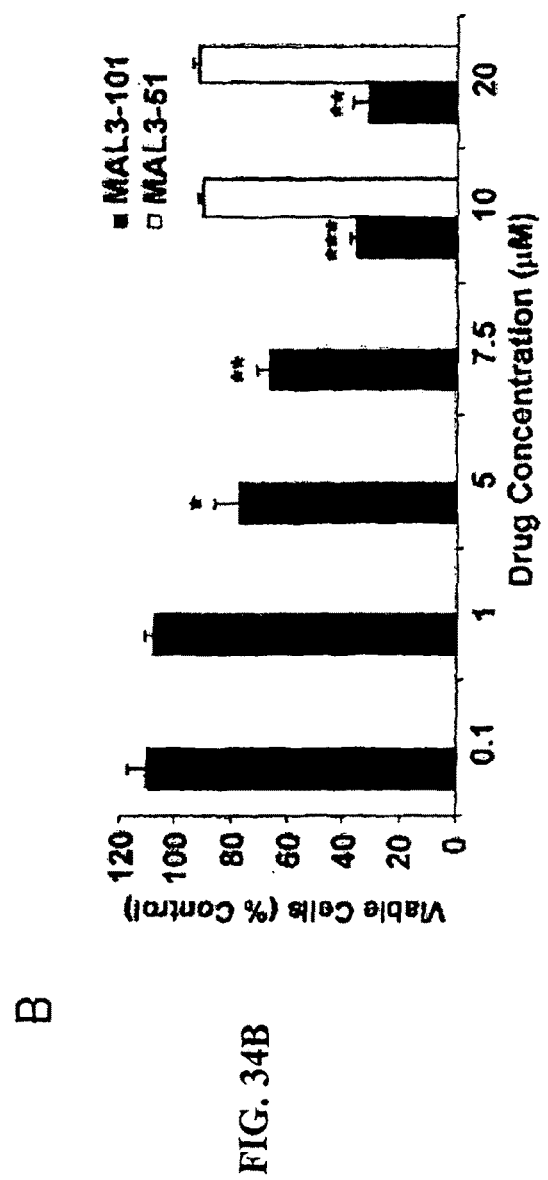
FIG. 34B depicts a graph of MM cell line NCI-H929 exposed to the indicated concentrations of MAL3-101 or MAL3-51 for 40 h and the percent viability compared to control, DMSO-treated cells as assessed by an MTS assay.

FIGS. 34A and 34B are experimental data summaries which depict that Hsp70 inhibitor MAL3-101 induces a graded cytotoxic effect in the multiple myeloma (MM) cell lines. In FIG. 34A, MM cell lines (1×10⁵) were exposed to 10 µM MAL3-101 for the indicated culture periods, and the fold change in percent viable cells in treated versus control cells was determined by an MTS assay. In FIG. 34B, NCI-H929 were exposed to the indicated concentrations of MAL3-101 or MAL3-51 for 40 h and the percent viability compared to control, DMSO-treated cells was assessed by an MTS assay. Data are presented as means and standard deviations (SDs) from three independent experiments; *P<0.05, P<0.01, *P<0.001.

As suggested by the dose response experiments utilizing MTS, exposure to MAL3-101 caused maximum induction of apoptosis in NCI-H929 (FIG. 35A). Since MAL3-101 initiates apoptosis though its ability to arrest the cell cycle, and by cleavage of caspase-3 and PARP in breast cancer cells. Next these features were examined in NCI-H929. FACS analysis showed that exposure to 10 µM MAL3-101 produced a time-dependent increase in apoptosis (FIG. 35A) and inhibition of cell cycle progression as indicated by a nearly 3-fold increase in the sub-$G_0/G_1$ phase and a 2.5-fold decrease in cells in the $G_2/M$ phase within 48 h of culture (FIG. 35B). This result was supported by Western immunoblotting analysis showing a time-dependent increase in the cleavage of caspase-3 and PARP after exposure to MAL3-101 (FIG. 35C). Taken together, these results indicate that MAL3-101 alone is capable of inhibiting MM tumor growth, with substantially greater efficacy against some lines than others.

FIGS. 35 A, 35B, and 35C depict that MAL3-101 induces cell cycle arrest and caspase-mediated apoptosis in the multiple myeloma (MM) cell line NCI-H929. FIG. 35A shows a time course chart of MM cell lines which were exposed to 10 µM of MAL3-101 for 40 h and the fold change in apoptosis in MAL3-101-treated versus control, DMSO-treated cells was determined by flow cytometry. Data are presented as means and SDs from three independent experiments; *P<0.05. FIG. 35B shows the percentages of NCI-H929 cells in the $G_0/G_1$ and $G_2/M$ phases of the cell cycle, as indicated in each panel. This result is representative of three independent experiments that yielded similar results. FIG. 35C depicts the results when NCI-H929 cells were exposed to 10 µM MAL3-101 for the indicated culture periods and immunoblotted with primary antibodies to detect caspase-3 and poly (ADP-ribose) polymerase (PARP), and, to ensure equal loading, β-actin. Bands corresponding to intact and cleaved caspase-3 and PARP are indicated. The data are representative of 4 experiments. FIGS. 35A, 35B, 35C are derived from the same experiment, which was performed to explore the way (i.e. mechanism) in which MAL3-101 mediates its anti-myeloma effects to kill myeloma cells. The cell lines (3 types of cell lines (NCI, RPMI, U266) indicated in FIG. 35A were cultured with MAL3-101 or without MAL3-101. These cells were analyzed for: MAL3-101-induced cell death (FIG. 35A); cell cycle progression (35 B), which shows that MAL3-101 arrested the growth of the myeloma cells (as shown for NCI-H929 cells); and for the presence of proteins that confirm cell death (35C), which shows that in fact there was protein evidence for cell death induced by MAL3-101 on myeloma cells (as shown for NCI-H929 cells).

Exposure to MAL3-101 Enhances the Antimyeloma Effects of MG-132:

Proteasome inhibition results in accumulation of aggregation-prone proteins, including unassembled IG (immunoglobulin) heavy and light chains, that induce apoptosis. Therefore, we questioned whether MAL3-101 would potentiate the antimyeloma effect of proteasome inhibition. When NCI-H929 were simultaneously exposed to a range of concentrations of MAL3-101 and MG-132 alone and in combination, it was found that their combination at equal concentrations significantly reduced the $IC_{50}$ (0.008 µM) compared to single agent MAL3-101 (and 8.3 µM) or MG-132 ($IC_{50}$ 1.7 µM) (FIG. 36A, and FIG. 40).

FIG. 36A through 36D depicts that MAL3-101 and MG-132 exhibit synergistic, cytotoxic effects on multiple myeloma tumor cells and endothelial progenitor cells. In FIG. 36A, NCI-H929 cells (1×10⁵) were exposed to the indicated concentrations of MAL3-101, MG-132, or a combination for 40 h and survival was assessed by an MTS assay; representative data from one of three independent experiments are shown; error bars represent SDs from replicate data points. Apparent absence of error bars indicates minimal variance. This result is representative of three independent experiments that yielded similar results. FIG. 36B depicts the fraction of non-viable cells compared to control, DMSO-treated cells in this experiment was used for isobologram analysis, where combination index (CI) values <1 indicate synergy. FIG. 36C depicts bone-marrow-derived tumor cells (black bars) and confluent endothelial progenitor cells (EPCs) (white bars) from multiple myeloma patients were exposed to the indicated concentrations of MAL3-101, MG-132, or their combination, and survival was assessed by an MTS assay. Dunnett's test, after significant one-way repeated-measures analyses of variance (P=0.004 and 0.002 for tumor cells and EPCs, respectively), compared control values to cell viability in the MAL3-101, MG-132, and MAL3-101+MG-132 conditions (*P≤0.05, **P≤0.001). FIG. 36D depicts the normal peripheral blood mononuclear cells (PBMC, black bars), bone marrow mononuclear cells (BMMC, gray bars), and confluent bone-marrow-derived EPCs (white bars) were exposed to the indicated concentrations of MAL3-101, MG-132, or a combination, and survival was assessed by an MTS assay.

Notably, when examined alone, each compound was ineffective at concentrations that gave rise to their combined $IC_{50}$. In fact, the synergistic action of MAL3-101 and MG-132 occurred over a range of concentrations (0.01-0.1 µM), and this was confirmed by CI values of 0.1 or less (FIG. 36B), indicating very strong synergism in their inhibition of MM cell growth. As expected, a synergistic increase in apoptosis was also observed in NCI-H929 exposed to a combination of the two compounds (FIG. 41).

Synergistic antimyeloma effects of MAL3-101 and MG-132 were confirmed in primary MM cells as well. As shown in FIG. 36C, viability of MM cells extracted from the BM was reduced by 33±8% (P=0.02) and 44±10% (P=0.07), respectively, by MAL3-101 and MG-132 and further decreased by 75±4% (P=0.001) by their combination. In addition to its effects on tumor cells, combined treatment with MAL3-101 and MG-132 also exerted potent synergistic cytotoxic effects on the MM microenvironment. As shown in FIG. 36C (white bars), viability of EPCs was reduced by 10±14% (P=0.7) and 16±17% (P=0.3), respectively, by MAL3-101 and MG-132, and further decreased by 60±7% (P=0.001) by their combination. The specificity of MAL3-101's effect on MM tumor and microenvironment was indicated by a lack of cytotoxicity in normal control BM, PBMC, and EPC populations (FIG. 36D).

Figure 41:
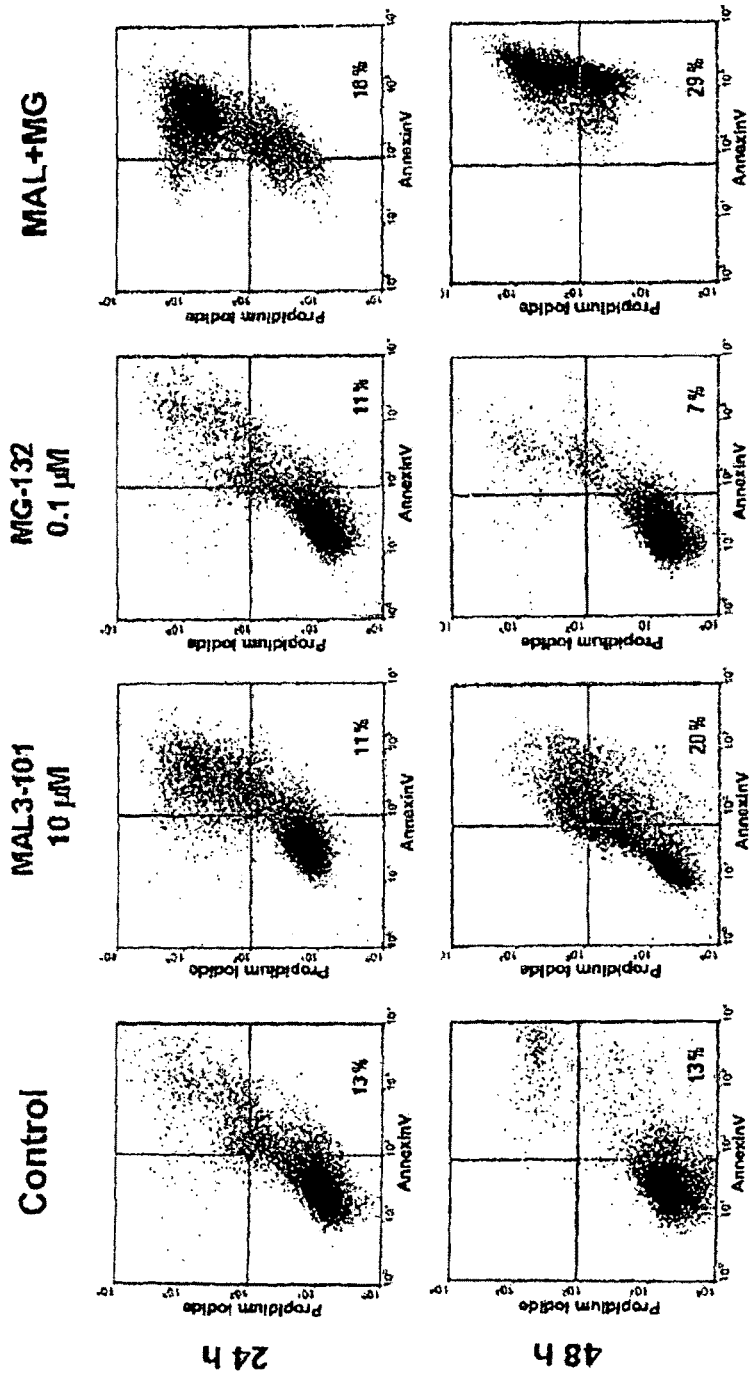
FIG. 41 illustrates that the exposure to MAL3-101 sensitizes MM cells to the cytotoxic effects of proteasome inhibition.

FIG. 41 illustrates that the exposure to MAL3-101 sensitizes MM cells to the cytotoxic effects of proteasome inhibition. NCI-H929 cells ($1 \times 10^5$) were exposed to the indicated concentrations of MAL3-101, MG-132, or their combination, and apoptosis was evaluated after 24 and 48 h of exposure by dual Annexin V and propidium iodide staining determined by flow cytometry. The proportion of total cells undergoing apoptosis initiation is shown in the lower right quadrant of each dot plot as Annexin V-positive, PI-negative cells. Representative dot plots from one of three experiments are shown.

Figures 37A, 37B:
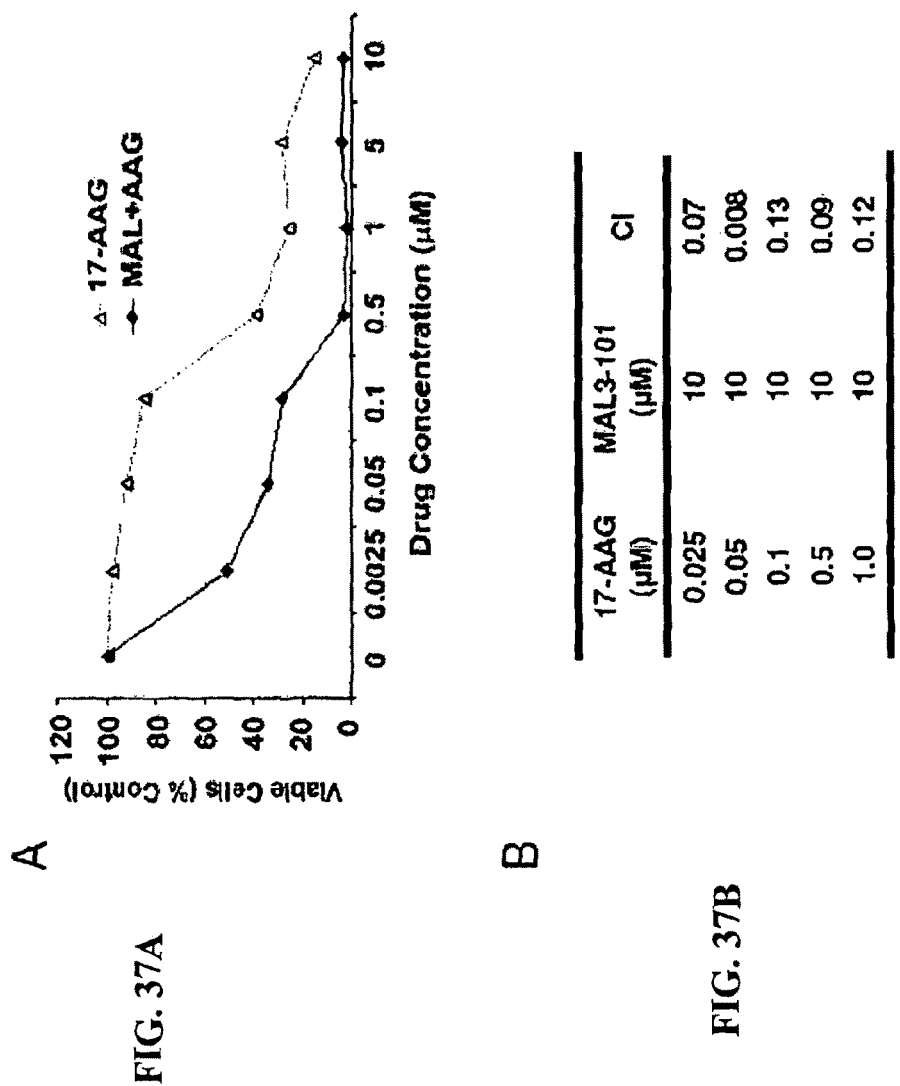
FIG. 37A shows percent viable cells as the NCI-H929 ($1 \times 10^5$) line was exposed to 17-AAG alone or in combination with 10 μM of MAL3-101 for 40 h and survival was assessed by an MTS assay. Representative data from one of three experiments are shown and error bars represent SDs from replicate data points.
FIG. 37B depicts the fraction of non-viable cells compared to control, DMSO-treated cells; data are depicted for isobologram analysis, where combination index (CI) values <1 indicate synergy.

Because Hsp90, another molecular chaperone, has destabilizing effects on oncoproteins and helps maintain MM cell homeostasis, next the effect of Hsp70 inhibition on antimyeloma effects of Hsp90 inhibitor, 17-AAG was addressed. When NCI-H929 cells were simultaneously exposed to MAL3-101 at close to the $IC_{50}$ (10 μM) and increasing concentrations of the Hsp90 inhibitor 17-AAG, alone and in combination for 40 h, it was found that combination of MAL3-101 and 17-AAG, decreased the $IC_{50}$ for 17-AAG from 0.4 μM to 0.03 μM (FIG. 37A and FIG. 40). These results are consistent with the prediction that antimyeloma effects of Hsp90 inhibition, which causes upregulation of Hsp70 gene expression, would be potentiated by simultaneous inhibition of Hsp70.

FIGS. 37A and 37B depicts that MAL3-101 and 17-AAG exhibit synergistic, cytotoxic effects on the MM cell line NCI-H929. FIG. 37A shows that as the NCI-H929 ($1 \times 10^5$) was exposed to 17-AAG alone or in combination with or 10 μM of MAL3-101 for 40 h and survival was assessed by an MTS assay. Representative data from one of three experiments are shown and error bars represent SDs from replicate data points. Apparent absence of error bars indicates minimal variance. FIG. 37B depicts the fraction of non-viable cells compared to control, DMSO-treated cells in this experiment was used for isobologram analysis, where combination index (CI) values <1 indicate synergy.

FIG. 40 is a table depicting the comparison of the inhibitory concentration (IC) of MAL3-101 with other modulators of protein quality control (MG-132 and 17-AAG) alone and in combination in the multiple myeloma cell line NCI-H929. $IC_{50}$ values for MAL3-101, MG-132, 17-AAG, and the indicated combinations represent the concentrations of these agents that reduced the viability of NCI-H929 by 50% after 40 h compared to control, DMSO-treated cells.

To begin to examine how these compounds, individually and in combination, impact the viability of NCI-H929, we asked whether the unfolded protein response (UPR) was induced following their administration. Under conditions of ER-stress, and UPR induction, mRNA of the transcription factor X-box binding protein 1 (XBP-1) is spliced resulting in the translation of a 54 kDa, XBP-1s isoform rather than the 33 kDa, XBP-1u isoform. The spliced isoform is essential for plasma cell differentiation and possibly MM progression [as described in N. N. Iwakoshi, A. H. Lee, P. Vallabhajosyula, K. L. Otipoby, K. Rajewsky, L. H. Glimcher, Plasma cell differentiation and the unfolded protein response intersect at the transcription factor XBP-1, Nat Immunol 4 (2003) 321-329 and D. R. Carrasco, K. Sukhdeo, M. Protopopova, R. Sinha, M. Enos, D. E. Carrasco, M. Zheng, M. Mani, J. Henderson, G. S. Pinkus, N. Munshi, J. Horner, E. V. Ivanova, A. Protopopov, K. C. Anderson, G. Tonon, R. A. DePinho, The differentiation and stress response factor XBP-1 drives multiple myeloma pathogenesis, Cancer Cell 11 (2007) 349-360, which are incorporated herein by reference], and XBP-1 splicing represents a sensitive, quantifiable read-out for the UPR.

Figures 38A, 38B:
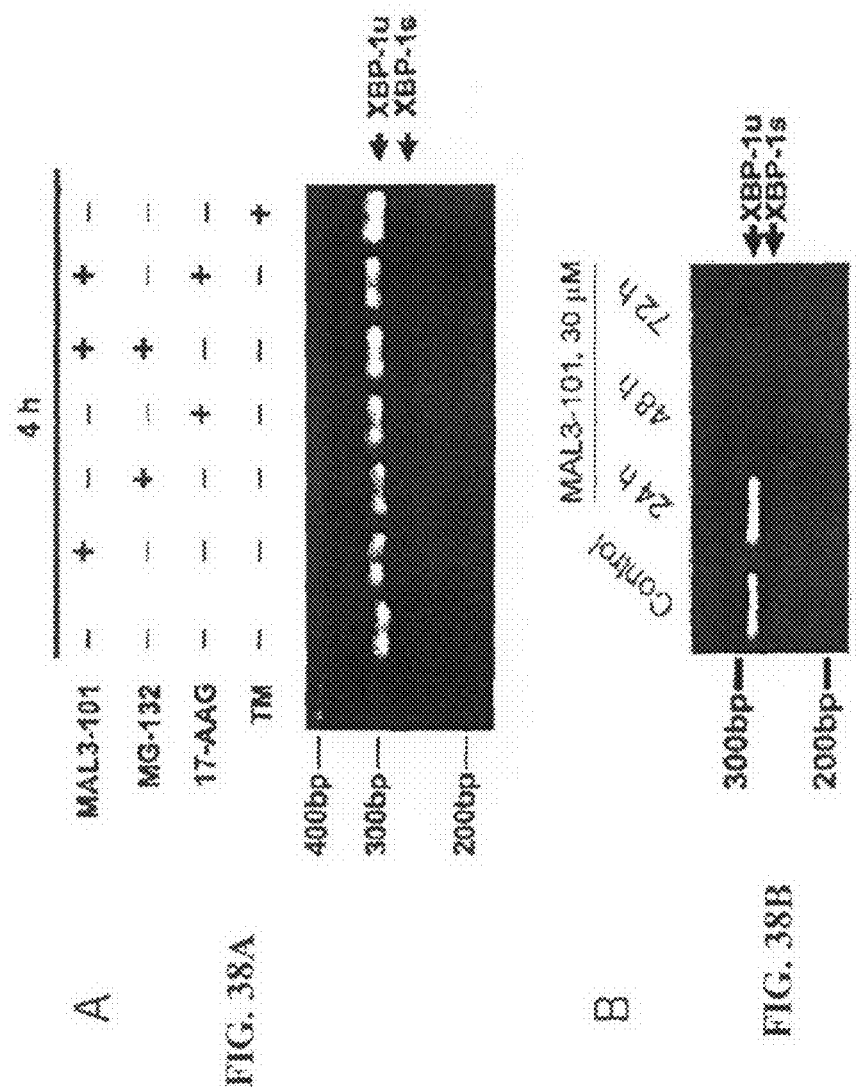
FIG. 38A shows the experimental results when NCI-H929 cells were exposed for 4 h to MAL3-101, MG-132, 17-AAG, or the indicated combination of the compounds, and total RNA was extracted for RT-PCR amplification. NCI-H929 treated for 4 h with 5 μg/ml tunicamycin (TM) as a positive control induced XBP-1 mRNA splicing ("XBP-1s"), indicating induction of the unfolded protein response and denoted by arrows on the right.
FIG. 38B shows the experimental results when NCI-H929 cells were exposed for various times, including 0 h, 24 h, 48 h, and 72 h to 30 μM MAL3-101 and total mRNA was extracted for RT-PCR amplification, as in FIG. 38A.

At relatively early time points when UPR induction is expected, no XBP-1 mRNA splicing was observed after exposure of NCI-H929 to MAL3-101, MG-132, or 17-AAG at concentrations that had resulted in synergistic cytotoxicity (FIG. 38A). However, at higher concentrations of MAL3-101 (30 μM, ~4-fold higher than the $IC_{50}$), and after 24 h of culture minimal XBP-1 mRNA splicing occurred (FIG. 38B), possibly as a result of absolute Hsp70 inhibition and functional impairment causing a block in translation, or nascent protein folding, and/or protein transit though the secretory pathway, or transcription. Consistent with these results, we found that the levels of the ER lumenal BiP chaperone, whose synthesis is enhanced by UPR activation, did not change in NCI-H929 exposed to MAL3-101, MG-132, and/or 17-AAG (data not shown).

FIG. 38A and FIG. 38B depict the unfolded protein response (UPR) is not induced in NCI-H929 in response to chaperone and/or proteasome inhibition. RT-PCR analysis was performed to assess XBP-1 mRNA splicing in NCI-H929, and arrows on the right indicate the 285 bp unspliced (XPB-1u) and the 259 bp spliced (XPB-1s) mRNA. FIG. 38A shows the experimental results when NCI-H929 cells were exposed for 4 h to MAL3-101, MG-132, 17-AAG, or the indicated combination of the compounds, and total RNA was extracted for RT-PCR amplification. NCI-H929 treated for 4 h with 5 μg/ml tunicamycin (TM) as a positive control induced XBP-1 mRNA splicing, indicated by arrows on the right. FIG. 38B shows the experimental results when NCI-H929 cells were exposed for 0, 24, 48, and 72 h to 30 μM MAL3-101 and total mRNA was extracted for RT-PCR amplification. Next the sensitivity of neoplastic MM cells to proteasome inhibition covaries with monoclonal IG production. Therefore, we studied IG trafficking in MAL3-101-treated MM cell lines. When intracellular and secreted IGs were quantitated, it was found that the relative amount of IG secretion was highest in the NCI-H929 which demonstrated highest sensitivity to MAL3-101-induced growth inhibition, compared to the U266 and RPMI-8226 which were less sensitive to MAL3-101 (FIG. 39). These data suggest that the measured sensitivity of MM cells to Hsp70 inhibition most likely arises from the added cellular stress of producing and secreting monoclonal IGs.

FIG. 39 is a table of experimental data which shows that the multiple myeloma cell line NCI-H929 is a high secretor of monoclonal immunoglobulin. Myeloma cell lines were grown at $1 \times 10^6$ cell/ml for 16 h, and 500 ng total protein from cell lysates and 500 ng from serum-free supernatants were used in ELISAs to determine intracellular and secreted light-chain (LC) levels, respectively. Relative LC secretion is shown as the fraction of secreted over intracellular LC. Data are presented as the mean±SD from 3 independent experiments.

Our observations indicate that MAL3-101 as a single agent or in combination with inhibitors of the cellular protein quality control machinery exerts significant antimyeloma effects on tumor and microenvironment in MM.

In MM, the protein folding machinery may be overloaded due to increased IG synthesis and secretion, and a significant population of the IGs may misfold; in fact, some MM cells produce unassembled IG single chains. The concentration of these proteins in the ER may be decreased by being retro-translocated back to the cytoplasm, where they are degraded by the proteasome, a process referred to as ER-associated degradation (ERAD). Since IGs fold in the ER and traffic through the secretory pathway, proteasome inhibition results in an increased load of misfolded proteins in the ER, thus triggering apoptosis. Because Hsp70 homologs in the ER and in the cytoplasm play critical roles in ERAD, synergistic, cytotoxic effects were observed on MM cell survival when the proteasome and Hsp70 were simultaneously inhibited. We also observed synergistic cytotoxicity in MM cells by combined inhibition of Hsp70 and Hsp90, further supporting the notion that MM cells are susceptible to treatments that compromise protein quality control.

The most MAL3-101-responsive cell line, NCI-H929, is a high secretor of monoclonal IG, indicating that IG load may correlate with sensitivity to inhibitors of the quality control machinery. The lack of UPR induction in MM cells may be triggered when both Hsp70 and the proteasome were inhibited since ERAD substrates should accumulate. Several factors may account for the failure of UPR induction by MAL-3 101, Hsp90, and proteasome inhibitors at concentrations that induced synergistic apoptosis: while NCI-H929 secrete IGs, they may lack the ability to sustain the UPR; or apoptosis may occur by pathways independent of UPR activation, including autophagy or aggresome disposal, therefore it will be important to better define at the molecular level the mechanisms that regulate inhibition of cell stress responses.

A critical result of our studies is the demonstration of synergistic effects of Hsp70 and proteasome inhibition on the MM microenvironment. Further, the inventors have demonstrated that IG gene rearrangement in MM EPCs, and thus protein misfolding and the ensuing ER stress response may determine the effects of Hsp70 and proteasome inhibition in these cells. This possibility is suggested by a lack of sensitivity to MAL3-101 in normal bone marrow, lymphocytes, and endothelial cells, most of which do not produce IG. Therefore, clinical application of MAL3-101 in MM may not only help overcome drug resistance by potentiating the effects of other inhibitors of protein quality control, but also by limiting MM growth via inhibition of tumor angiogenesis.

MAL3-101, a recently developed Hsp70 modulator, may provide a viable means of enhancing the antimyeloma effects individually and in combination with both of both proteasome and Hsp90 inhibition, thus potentially reducing drug resistance in MM. In addition to tumor, MAL3-101 also has effects on the microenvironment by targeting the microvasculature. Thus the various embodiments of the present invention employ MAL3-101 and other small molecule derivatives thereof, as an agent useful in the treatment of Hsp70 dependent cancer, specifically for multiple myeloma.

The experiments planned and carried out by the inventors of the present invention showed that MAL3-101, an inhibitor of Hsp70, killed myeloma cells by programmed cell death. This finding was confirmed in myeloma cell lines (myeloma cells that perpetually grow in culture, are commercially available, and are originally derived from patients) as well as in fresh cells obtained from patients with clinical multiple myeloma. The cytotoxic effects of MAL3-101 and therefore Hsp70 inhibition were observed in myeloma cells from patients and also on the microvascular environment (bone marrow) from patients with multiple myeloma environment. The microvascular forms blood vessels that feed and nurture the myeloma tumor cells; therefore, the death of these microvascular cells is also necessary for a potent anti-myeloma therapeutic effect.

Hsp70 inhibitors including—but not limited to the dihydropyrimidinones—may be employed with Hsp90 inhibitors and/or proteasome inhibitors. The combination of the various types of inhibitors exhibits the synergistic effects in treating cancerous cells as is provided in the embodiments and applications of the present invention. As discussed and described in reference to these embodiments, the synergistic effect refers to the interaction of two or more agents, such that their combined effect is greater than the sum of their individual effects. Thus, synergy refers to an enhanced treatment over the mere additive affect of treatment or therapies. Further to the present invention, synergy is the result (measured and demonstrated experimentally) of treating MM cells with an Hsp70 inhibitor in combination with at least one of a proteasome inhibitor and/or an Hsp90 inhibitor. The synergistic effect is demonstrated in the significant increase in apoptotic effect on MM cells exhibited with a combination treatment of very low concentrations of each of the inhibitors, as referenced in the Examples and shown in the FIGS. The low level concentrations of the inhibitors administered individually would likely result in ineffective treatment value and/or little therapeutic effect on MM cells. However, administered in combination, the resulting synergistic effect provides for a significantly increased effectiveness in the treatment of the cancerous cells. The Hsp70 inhibitor in combination with at least one of a proteasome inhibitor and/or an Hsp90 inhibitor provides for the cooperative interaction among the inhibitor classes which creates the enhanced combined effect demonstrated with the experimental examples section, as well as the embodiments of the present invention. This enhanced combined effect is an effective treatment of MM cells which have previously shown great resistance to treatments through, for example, the protection afforded to the cancer cells through the heat shock protein chaperoning mechanism (discussed previously). The present invention provides for various classes of inhibitors (including Hsp70 inhibitors, Hsp90 inhibitors, and proteasome inhibitors) to be administered to cancerous cells in very low concentrations, with the benefits of providing a cooperative synergistic force to enhance apoptotic effect in treating MM cells.

The Hsp70 inhibitor, MAL3-101, is an agent that may be used in the synergistic therapies provided with the present invention. MAL3-101, its derivatives, and other Hsp70 inhibitors provide a potent mechanism to effectuate the inhibition of Hsp70, and may therefore also be employed in combination treatments with, for example, proteasome inhibitors and/or Hsp90 inhibitors, which exhibit the synergistic apoptotic effect upon treatment of certain types of cancer cells (e.g. MM cells). The great synergy that is exhibited in the methods of combined treatments of the present invention is an important benefit and advantage in treating these certain types of cancer. That is, the synergy of the combined treatments allows for substantial dose reduction of each of the inhibitor drugs that are individually effective but may not be used in doses that are high enough to effectuate a prolonged response or cure because of the toxicity which results from large doses or continued doses over a prolonged period of time. For example, the proteasome inhibitor Bortezomib is used at most for about 10 months at limited dosages due to its toxicity. After the Bortezomib treatment, multiple myeloma may commonly relapse and due to accumulative side effects and toxicity, Bortezomib is not usable for subsequent treatments of the cancer.

MAL3-101 exhibits potent inhibitory effects on the proliferation and survival of MM cells, including primary tumor cells and EPCs (the microvasculature) obtained from MM patients. MAL3-101 also inhibits MM cell cycle progression and activates the intrinsic apoptotic pathway. Moreover, strong cytotoxic synergy exists between MAL3-101 and inhibitors of the proteasome and of Hsp90. These data suggest that by targeting the tumor and its vascular microenvironment, and by allowing dose reduction of synergistic agents without compromising effectiveness, Hsp70 inhibition will improve existing strategies to combat MM and circumvent treatment resistance Thus, when used in the combined, synergistic treatment with Hsp70 and/or Hsp90 inhibitors, Bortezomib and/or other proteasome inhibitors, may be used at much lower concentrations and for over much longer periods of time. The combined synergistic treatment may employ the use of Bortezomib treatments at lower concentrations for longer periods of time, while exhibiting effectiveness as a prolonged treatment of MM. The combined synergistic treatment may then be continued for longer periods of time while avoiding the known accumulative negative side effects and toxicity of inhibitors, including Bortezomib. As Hsp70 inhibitors potentiate lower concentrations of Bortezomib while reducing the chaperoning effect of Hsp70 upregulation in MM cells, Hsp70 inhibitors provide various benefits in effectively treating MM, relapse MM, and related cancers.

Various modifications and variations of the described apparatus and methods of the invention will be apparent to those skilled in the art without departing from the scope and spirit of the invention. Although the invention has been described in connection with specific embodiments, outlined above, it should be understood that the invention should not be unduly limited to such specific embodiments. Various changes may be made without departing from the spirit and scope of the invention as defined in the following claims.

What is claimed is:

1. A method of treating an Hsp70 dependent cancer, comprising:
   providing at least one Hsp70 dependent cancer cell;
   contacting the at least one cell with a sub-effective concentration of MAL3-101; and
   contacting the at least one cell with a sub-effective concentration of a proteasome inhibitor,
   wherein the sub-effective concentration of MAL3-101 and the sub-effective concentration of the proteasome inhibitor have a synergistic effect upon the at least one cell.

2. The method of claim 1, further comprising the step of contacting the at least one cell with an Hsp90 inhibitor.

3. The method of claim 2, wherein the Hsp90 inhibitor is 17-AAG.

4. The method of claim 1, wherein the Hsp70 dependent cancer is selected from the group consisting of: multiple myeloma, lung cancer, breast cancer, colon cancer, cervical cancer, and combinations thereof.

5. The method of claim 1, wherein the proteasome inhibitor is MG-132.

6. The method of claim 1, wherein the sub-effective concentration of MAL3-101 is from about 0.01 μM to about 0.1 μM.

7. The method of claim 1, wherein the sub-effective concentration of the proteasome inhibitor is from about 0.01 μM to about 0.1 μM.

* * * * *